(12) United States Patent
Schwartz et al.

(10) Patent No.: US 7,582,478 B2
(45) Date of Patent: Sep. 1, 2009

(54) CLEAVED SERUM RESPONSE FACTOR IN CARDIAC DIAGNOSIS AND THERAPY

(75) Inventors: Robert J. Schwartz, Houston, TX (US); Lei Wei, Pearland, TX (US); Jiang Chang, Houston, TX (US); Mark Entman, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 10/763,037

(22) Filed: Jan. 22, 2004

(65) Prior Publication Data

US 2004/0214771 A1  Oct. 28, 2004

Related U.S. Application Data

(60) Provisional application No. 60/441,668, filed on Jan. 22, 2003.

(51) Int. Cl.
*C12N 5/00* (2006.01)
*C12N 5/02* (2006.01)
*A61K 48/00* (2006.01)
*A61K 38/30* (2006.01)

(52) U.S. Cl. .................. 435/325; 514/12; 424/93.2; 424/93.6

(58) Field of Classification Search .............. None
See application file for complete search history.

(56) References Cited

U.S. PATENT DOCUMENTS 5,661,122 A   8/1997   Clark et al.

OTHER PUBLICATIONS

Narula et al. (PNAS. Jul. 1999. col. 96: 8144-8149).*
Drewett et al. (Journal of Biological Chemistry. 2001. vol. 276; No. 36: 33444-33451).*
Kang et al. (Circulation Research. 2000; 86: 1107-1113).*
Cohen (Biochemical Journal. 1997; 326: 1-15).*
Mets, "Anesthesia for left ventricular assist device placement"; J Cardiothorac Vasc Anesth; Jun. 2000; 316-326; vol. 14(3).
Chang et al., "Inhibitory Cardiac Transcription Factor, SRF-N, Is Generated by Caspase 3 Cleavage in Human Heart Failure and Attenuated by Ventricular Unloading"; Circulation; Jul. 2003; 407-413; vol. 108.
Belaguli et al., "Dominant Negative Murine Serum Response Factor: Alternative Splicing within the Activation Domain Inhibits Transactivation of Serum Response Factor Binding Targets", Molecular and Cellular Biology, Jul. 1999, 4582-4591, vol. 19(7).
Davis et al., "Increased expression of alternatively spliced dominant-negative isoform of SRF in human failing hearts", Am J Physiol Heart Circ Physiol, H1521-H1533, 2002, vol. 282, First published Dec. 20, 2001; doi:10.1152/ajpheart.00844.2001.

* cited by examiner

*Primary Examiner*—Janet L Epps-Smith
*Assistant Examiner*—Scott Long
(74) *Attorney, Agent, or Firm*—Jackson Walker L.L.P.

(57) ABSTRACT

The present invention is directed to the cleavage of serum response factor as it relates to cardiac disease. In specific embodiments, failing cardiac tissue is diagnosed in tissues comprising elevated cleavage of serum response factor. In further specific embodiments, heart failure is associated with cardiac myocyte apoptosis as a result of an increase in cleaved serum response factor, particularly by caspases.

10 Claims, 4 Drawing Sheets

SEQUENCE LISTING

<160> NUMBER OF SEQ ID NOS: 5

<210> SEQ ID NO 1
<211> LENGTH: 10
<212> TYPE: DNA
<213> ORGANISM: Human

```
<220> FEATURE:
<221> NAME/KEY: misc_feature
<222> LOCATION: (1)..(10)
<223> OTHER INFORMATION: N = A or T

<400> SEQUENCE: 1 ccnnnnnngg                                                              10

<210> SEQ ID NO 2
<211> LENGTH: 508
<212> TYPE: PRT
<213> ORGANISM: Human

<400> SEQUENCE: 2
```

| | | | | | | | | | | | | | | | |
|---|---|---|---|---|---|---|---|---|---|---|---|---|---|---|---|
| Met | Leu | Pro | Thr | Gln | Ala | Gly | Ala | Ala | Ala | Leu | Gly | Arg | Gly | Ser | |
| 1 | | | | 5 | | | | | 10 | | | | | 15 | |
| Ala | Leu | Gly | Gly | Ser | Leu | Asn | Arg | Thr | Pro | Thr | Gly | Arg | Pro | Gly | Gly |
| | | | 20 | | | | | 25 | | | | | 30 | | |
| Gly | Gly | Gly | Thr | Arg | Gly | Ala | Asn | Gly | Gly | Arg | Val | Pro | Gly | Asn | Gly |
| | | 35 | | | | | 40 | | | | | 45 | | | |
| Ala | Gly | Leu | Gly | Pro | Gly | Arg | Leu | Glu | Arg | Glu | Ala | Ala | Ala | Ala | |
| | 50 | | | | | 55 | | | | | 60 | | | | |
| Ala | Thr | Thr | Pro | Ala | Pro | Thr | Ala | Gly | Ala | Leu | Tyr | Ser | Gly | Ser | Glu |
| 65 | | | | | 70 | | | | | 75 | | | | | 80 |
| Gly | Asp | Ser | Glu | Ser | Gly | Glu | Glu | Glu | Leu | Gly | Ala | Glu | Arg | Arg | |
| | | | | 85 | | | | | 90 | | | | | 95 | |
| Gly | Leu | Lys | Arg | Ser | Leu | Ser | Glu | Met | Glu | Ile | Gly | Met | Val | Val | Gly |
| | | | 100 | | | | | 105 | | | | | 110 | | |
| Gly | Pro | Glu | Ala | Ser | Ala | Ala | Thr | Gly | Gly | Tyr | Gly | Pro | Val | Ser | |
| | | 115 | | | | | 120 | | | | | 125 | | | |
| Gly | Ala | Val | Ser | Gly | Ala | Lys | Pro | Gly | Lys | Lys | Thr | Arg | Gly | Arg | Val |
| | 130 | | | | | 135 | | | | | 140 | | | | |
| Lys | Ile | Lys | Met | Glu | Phe | Ile | Asp | Asn | Lys | Leu | Arg | Arg | Tyr | Thr | Thr |
| 145 | | | | | 150 | | | | | 155 | | | | | 160 |
| Phe | Ser | Lys | Arg | Lys | Thr | Gly | Ile | Met | Lys | Lys | Ala | Tyr | Glu | Leu | Ser |
| | | | | 165 | | | | | 170 | | | | | 175 | |
| Thr | Leu | Thr | Gly | Thr | Gln | Val | Leu | Leu | Leu | Val | Ala | Ser | Glu | Thr | Gly |
| | | | 180 | | | | | 185 | | | | | 190 | | |
| His | Val | Tyr | Thr | Phe | Ala | Thr | Arg | Lys | Leu | Gln | Pro | Met | Ile | Thr | Ser |
| | | | 195 | | | | | 200 | | | | | 205 | | |
| Glu | Thr | Gly | Lys | Ala | Leu | Ile | Gln | Thr | Cys | Leu | Asn | Ser | Pro | Asp | Ser |
| | 210 | | | | | 215 | | | | | 220 | | | | |
| Pro | Pro | Arg | Ser | Asp | Pro | Thr | Thr | Asp | Gln | Arg | Met | Ser | Ala | Thr | Gly |
| 225 | | | | | 230 | | | | | 235 | | | | | 240 |
| Phe | Glu | Glu | Thr | Asp | Leu | Thr | Tyr | Gln | Val | Ser | Glu | Ser | Asp | Ser | Ser |
| | | | | 245 | | | | | 250 | | | | | 255 | |
| Gly | Glu | Thr | Lys | Asp | Thr | Leu | Lys | Pro | Ala | Phe | Thr | Val | Thr | Asn | Leu |
| | | | 260 | | | | | 265 | | | | | 270 | | |
| Pro | Gly | Thr | Thr | Ser | Thr | Ile | Gln | Thr | Ala | Pro | Ser | Thr | Ser | Thr | Thr |
| | | 275 | | | | | 280 | | | | | 285 | | | |
| Met | Gln | Val | Ser | Ser | Gly | Pro | Ser | Phe | Pro | Ile | Thr | Asn | Tyr | Leu | Ala |
| | 290 | | | | | 295 | | | | | 300 | | | | |
| Pro | Val | Ser | Ala | Ser | Val | Ser | Pro | Ser | Ala | Val | Ser | Ser | Ala | Asn | Gly |
| 305 | | | | | 310 | | | | | 315 | | | | | 320 |
| Thr | Val | Leu | Lys | Ser | Thr | Gly | Ser | Gly | Pro | Val | Ser | Ser | Gly | Gly | Leu |
| | | | | 325 | | | | | 330 | | | | | 335 | |

```
Met Gln Leu Pro Thr Ser Phe Thr Leu Met Pro Gly Gly Ala Val Ala
                340                 345                 350

Gln Gln Val Pro Val Gln Ala Ile Gln Val His Gln Ala Pro Gln Gln
            355                 360                 365

Ala Ser Pro Ser Arg Asp Ser Thr Asp Leu Thr Gln Thr Ser Ser
        370                 375                 380

Ser Gly Thr Val Thr Leu Pro Ala Thr Ile Met Thr Ser Ser Val Pro
385                 390                 395                 400

Thr Thr Val Gly Gly His Met Met Tyr Pro Ser Pro His Ala Val Met
                405                 410                 415

Tyr Ala Pro Thr Ser Gly Leu Gly Asp Gly Ser Leu Thr Val Leu Asn
                420                 425                 430

Ala Phe Ser Gln Ala Pro Ser Thr Met Gln Val Ser His Ser Gln Val
            435                 440                 445

Gln Glu Pro Gly Gly Val Pro Gln Val Phe Leu Thr Ala Ser Ser Gly
        450                 455                 460

Thr Val Gln Ile Pro Val Ser Ala Val Gln Leu His Gln Met Ala Val
465                 470                 475                 480

Ile Gly Gln Gln Ala Gly Ser Ser Ser Asn Leu Thr Glu Leu Gln Val
                485                 490                 495

Val Asn Leu Asp Thr Ala His Ser Thr Lys Ser Glu
                500                 505

<210> SEQ ID NO 3
<211> LENGTH: 4201
<212> TYPE: DNA
<213> ORGANISM: Human

<400> SEQUENCE: 3
ggtcggggga tccctccgcc gccagcgcgt ggtcccggcc ccctccaccc gccgtctcgg      60
ccgcggccag cagcccctgc cccccggggg acgctgacgg ccgcccggcg cgccgcccta     120
gcagacggac agggggcgct gcgcgcggcc tgggcaacc  cgggccacag gggcaggaaa     180
gtgagggccc aggtcggccc gggcgtgcag gggccccggg ttcgcagcgg cggccgcggc     240
agcgatagcg gcactagcag cagcgggagt gccgggttga gccgggaagc cgatggcggc     300
ggctgcggcg gctccgattc ctcgctgact gcccgtccgc cctcctgcat cgagcgccat     360
gttaccgacc caagctgggg ccgcggcggc tctgggccgg ggctcggccc tggggggcag     420
cctgaaccgg accccgacgg ggcggccggg ccgcggcggc gggacacgcg gggctaacgg     480
gggccgggtc cccgggaatg cgcgcgggct cgggcccggc cgcctggagc gggaggctgc     540
ggcagcggcg gcaaccaccc cggcgcccac cgcgggggcc ctctacagcg gcagcgaggg     600
cgactcggag tcgggcgagg aggaggagct gggcgccgag cggcgcggcc tgaagcggag     660
cctgagcgag atgagatcg  gtatggtggt cggtgggccc gaggcgtcgg cagcggccac     720
cgggggctac gggccggtga gcggcgcggt gagcggggcc aagcccggta agaagacccg     780
gggccgcgtg aagatcaaga tggagttcat cgacaacaag ctgcggcgct acacgacctt     840
cagcaagagg aagacgggca tcatgaagaa ggcctatgag ctgtccacgc tgacagggac     900
acaggtgctg ttgctggtgg ccagtgagac aggccatgtg tataccttg  ccacccgaaa     960
actgcagccc atgatcacca gtgagaccgg caaggcactg attcagacct gcctcaactc    1020
gccagactct ccaccccgtt cagacccac  aacagaccag agaatgagtg ccactggctt    1080
tgaagagaca gatctcacct accaggtgtc ggagtctgac agcagtgggg agaccaagga    1140
```

-continued

```
cacactgaag ccggcgttca cagtcaccaa cctgccgggt acaacctcca ccatccaaac    1200
agcacctagc acctctacca ccatgcaagt cagcagcggc ccctcctttc ccatcaccaa    1260
ctacctggca ccagtgtctg ctagtgtcag ccccagtgct gtcagcagtg ccaatgggac    1320
tgtgctgaag agtacaggca gcggccctgt ctcctctggg ggccttatgc agctgcctac    1380
cagcttcacc ctcatgcctg gtggggcagt ggcccagcag gtcccagtgc aggccattca    1440
agtgcaccag gccccacagc aagcgtctcc ctcccgtgac agcagcacag acctcacgca    1500
gacctcctcc agcgggacag tgacgctgcc cgccaccatc atgacgtcat ccgtgcccac    1560
aactgtgggt ggccacatga tgtaccctag cccgcatgcg gtgatgtatg cccccacctc    1620
gggcctgggt gatggcagcc tcaccgtgct gaatgccttc tcccaggcac catccaccat    1680
gcaggtgtca cacagccagg tccaggagcc aggtggcgtc cccaggtgt tcctgacagc    1740 atcatctggg acagtgcaga tccctgtttc agcagttcag ctccaccaga tggctgtgat    1800
agggcagcag gccgggagca gcagcaacct caccgagcta caggtggtga acctggacac    1860
cgcccacagc accaagagtg aatgatccgc ccgccgccct ggacagatgg cccaagggat    1920
ggcaccactt atttattgtt gccttttcac gttttctta cacacacgtt gacgggccgc    1980
aggagggagg cggggaggag gaacgggcag ccacaggact gagccctctc actccagcca    2040
aagaaatggg cctgcctgcc tccacccgtc ctccctcagc ctccccttct tcccgcccca    2100
cctcccattt ctgttgctgg aggggctgtc ctccttcctg ggaccccctc gccagcttgg    2160
ctcgatgttt gccatgagta ttagcttacc caatgggacc gtgccccacc tcccacaca    2220 caggccttct gtggggctgg gcaccgtgtc ctcctctgag gaagcagttg gggccctctt    2280
gccagcctcc ttgctgaccc caggtcagcc ctgtgtctgt cacaggctgg gtcaaaagag    2340
ccctggctct gcccctcagg gggccagctg gggagatggg ggcttcttcc tcacactgct    2400
gtcctctccc ccttcagctc ctgagtagct gggcctgtgc actgggcagg ttcctggggc    2460
cgcctgccct gccttgccgc tccccttgga cctccagggg ctcctgggtt ggagggaacc    2520
accagcgttc ccttctcccc cttgtcttcc ccctctcct cccagctgct ttacttaaag    2580
ttgattttga acttttatt tgaggagacg aagtgaaaac aaatctataa atatatattt    2640
ttaaaatatt taacttttt ttatggcgtt tttctcgtcc ccctccctgc ccaaactccc    2700
cttccctggg gagccctcag gctccccaga actggctggg ccctggggga cagagccacc    2760
ccatgagctc ggggtccacc agtgtgtggg ggagattctg ggtttgccca gtcctggatt    2820
gtttccagga gaaagccggg ggaggggccc tcaggccatt cccaacggg gtggggaggg    2880 tgacccacag ctctgggcct cttttttgccc tttaggctg ttgctaggga gagggaagag    2940
ggagaccaaa tgtcggggtt gggtggagg ggcgtcaggc agaggcaact gacttcattt    3000
gtgccacacg catgggcatt gcagccttgc gctgtcccag gcatgcagct gcctggggcc    3060
caagttgcag tgagcagggt gggtctggg aggggtgag aggcaggaat gggggtcaga    3120
agaagtggga gcagcttctt gggctgagtg cagccaaagg ggagccagaa atgggcagtt    3180
ctcccaggga gtgagcagct actgtaactt ttttaaatta agacaaaag ccttgaagaa    3240 aatgacttta tttttctaag tgtaacctca gtatttatgt aatttgtaca ggggccatgc    3300 cccaccccc tcctcccct ttggggtaga ccttgagggt gggccagcat aggggggagg    3360
gtcttttacc ctgtgtcaga gcctaccttc accacctata tccagaaggg gagcttttc    3420 agaaacaggg cagcagtggg gtgaaatttt cttaacccct aagactgcct tcagtaggaa    3480
caagctggct tctgtgatta ggtgaaggga tgggggaaga ttttatgcac agcctagtta    3540
```

```
tcaaggggat gatttgccga catgtttgag aacccccta cctctaaccc tcattgctgt    3600
cttgccccag tttggggtgc caagatggaa gtcacctttc tgggctttct cctggagact    3660
agctggggct tatgggtggc tttcaaggct ggggcatggc aaatcagggg ccagagagca    3720
ggggagcttg ggactcaggt ctgtaactgc ccagcccctt ttctctgctc ttgtttcact    3780
ccaccatcac tcactcactc cccactcccc cacccatggg gaggagacct ttgatgaatt    3840
cttcctctcc ttcccacaaa agacagaccc agtgagtgaa tcaggcaaag tgcttataat    3900
gtgtgttgtg tgagcgtggc cttgggagga catgcgtgtg tcagggatga gttgaggtga    3960
tatttttatg tgcagcgacc cttggtgttt cccttcctcg gtggctctgg ggtatgtgtg    4020
tgtgggtgtg tgcgcctgag tgagtgtgtg tgcttgaatg tgagtgtgta tgtcagtggt    4080
ttctacttcc cctgggatgc tgacccagga atagtggaca tggtcacagt cctatgtaca    4140
gagctttctt ttgtattaaa aaaaaatact ctttcaataa atgtatcatt tttgtgcaca    4200
g                                                                   4201

<210> SEQ ID NO 4
<211> LENGTH: 358
<212> TYPE: DNA
<213> ORGANISM: Artificial Sequence
<220> FEATURE:
<223> OTHER INFORMATION: Promoter

<400> SEQUENCE: 4
gagctccacc gcggtggcgg ccgtccgccc tcggcaccat cctcacgaca cccaaatatg     60
gcgacgggtg aggaatggtg gggagttatt tttagagcgg tgaggaaggt gggcaggcag    120
caggtgttgg cgctctaaaa ataactcccg ggagttattt ttagagcgga ggaatggtgg    180
acacccaaat atggcgacgg ttcctcaccc gtcgccatat ttgggtgtcc gccctcggcc    240
ggggccgcat tcctggggc cgggcggtgc tcccgcccgc ctcgataaaa ggctccgggg    300
ccggcggcgg cccacgagct acccggagga gcgggaggcg ccaagctcta gaactagt     358

<210> SEQ ID NO 5
<211> LENGTH: 12
<212> TYPE: PRT
<213> ORGANISM: Human

<400> SEQUENCE: 5

Gly Ala Asn Gly Gly Arg Val Pro Gly Asn Gly Ala
1               5                   10
```

CLEAVED SERUM RESPONSE FACTOR IN CARDIAC DIAGNOSIS AND THERAPY

This application claims priority to U.S. Provisional Patent Application Ser. No. 60/441,668, filed Jan. 22, 2003, incorporated by reference herein in its entirety.

FIELD OF THE INVENTION

The present invention relates to the fields of cell biology, molecular biology, and medicine. Specifically, the invention is directed to diagnosis of cardiac disease and/or cardiac failure. More specifically, the invention is directed to cardiac disease therapy.

BACKGROUND OF THE INVENTION

Heart failure is the leading cause of combined morbidity and mortality in the United States and other developed industrial nations. It remains an incurable disease process with an estimated two-year mortality of 30-50% for the patients with advanced disease. Although great advances in the treatment for failing heart have been made, the understanding of the molecular mechanism leading to heart failure is still limited. It is evident, however, that severe heart failure is associated with striking decreases in the expression of cardiac specific genes (Razeghi et al., 2002; Hwang et al., 2002; Barrans et al., 2002).

Serum response factor (SRF) is a muscle enriched transcription factor, which plays an important role in the regulation of contractile protein gene expression in mammalian heart. SRF serves as a platform to recruit and interact with other muscle regulatory proteins, such as Nkx-2.5 (Chen et al., 1996) and GATA4 (Sepulveda et al., 1996), and it is also obligate for normal muscle gene transcription. Expression of mutated SRF in transgenic mice can lead to severely dilated cardiomyopathy (Zhang et al., 2001).

SRF is a member of an ancient DNA binding protein superfamily, whose evolutionarily divergent relatives share a highly conserved DNA-binding/dimerization domain of 90 amino acids, termed the MADS box, named after four proteins (MCM1, Agamous, Deficiens, and SRF). The regulatory regions of a number of muscle specific genes such as skeletal, cardiac and smooth muscle α-actin, and other myogenic specified genes contain serum response elements (SRE; an example of which is provided in SEQ ID NO:1), which are required for promoter activity and depend upon SRF for activity (Lee et al., 1992; Li et al., 1997). Mutations that prevent SRF binding severely impair the expression of c-fos, as well as these muscle-restricted promoter (Boxer et al., 1989; Lee et al., 1991). High levels of SRF expression and increased SRF mass appear to coincide with the expression of muscle a actins, noted as early markers for terminal striated and smooth muscle differentiation (Croissant et al., 1996; Belaguli et al., 1997). SRF also serves as a platform to recruit other cardiac enriched transcription factors to activate cardiac specific genes (Belaguli et al., 2000; Chen and Schwartz, 1996). The recent analysis of SRF null mutants revealed an absoulate dependence for SRF for the formation of embryonic cardiogenic mesoderm (Arsenien et al., 1998). Expression of the mutated SRF in transgenic mice can lead to severely dilated cardiomyopathy (Zhang et al., 2001). Taken together, these studies clearly support an obligatory role for SRF as an obligatory myogenic transcription factor.

Apoptosis, or programmed cell death, is an evolutionarily conserved process by which unwanted or damaged cells are removed in order to keep tissue or body homeostasis. When deregulated, apoptosis can result in a number of human diseases including inflammation, cancer and neurodegenerative disease. Apoptosis is associated with the activation of serial caspases in proteolytic cascade after exposure to apoptotic signals (Scarabelli et al., 2002; Scarabelli et al., 2001; Gottlieb et al., 1994). Caspase activation could mediate the cleavage of vital proteins (Sebbagh et al., 2001; Emoto et al., 1995; Moretti et al., 2002) and lead to varied pathogenesis. In fact, caspase 3 activation in apoptotic cultured cells led to SRF cleavage (Drewett et al., 2001; Bertolotto et al., 2000). Recently, heart failure has been associated with cardiac myocyte apoptosis (Kang and Izumo, 2000; Haunstetter and Izumo, 1998; Hirota et al., 1999; Zhang et al., 2000). The loss of functional myocytes via cell apoptosis pathway appears to play an important role in the progression of cardiac failure. With regard to heart failure, the implicit assumption has been that weak activation of the proteolytic cascade associated with caspase leads inexorably toward apoptosis with eventual heart failure arising from myocyte loss (Kang and Izumo, 2000; Haunstetter and Izumo, 1998; Hirota et al., 1999; Narula et al., 1999; Narula et al., 1996; Narula et al., 1998; Narula et al., 1997).

BRIEF SUMMARY OF THE INVENTION

The present invention is directed to a system, method, and compositions related to diagnosis of cardiac failure and/or cardiac disease associated with, or comprising, elevated levels of cleaved serum response factor, particularly by caspases during apoptosis. In specific embodiments, the cleavage of SRF is diagnosed, prevented, ameliorated (although not necessarily completely), inhibited (although not necessarily completely), or a combination thereof. In specific embodiments, the cleavage of SRF is inhibited, prevented, or ameliorated partially.

Two recent studies (Bertolotto et al., 2000; Drewett et al., 2001) have shown that SRF is the target protein for caspase 3 and caspase 7 and can be cleaved during apoptosis in cultured cells. Two major fragments were observed with similar molecular weight at 30 kD. The fragments of cleavage lost SRF transcriptional activity. Moreover, the cleavage of SRF resulted in an inhibition of the c-fos promoter transcriptional activity. Caspase inhibitors can prevent SRF from cleavage and abolish the inhibitory effect on the c-fos promoter transcriptional activity (Bertolotto et al., 2000; Drewett et al., 2001).

Known molecular mechanisms leading to heart failure are still limited, but reduced gene activity and activation of caspase 3 are hallmarks of end-stage heart failure. The present inventors accurately postulated that caspase 3 cleavage of SRF plays a dominant inhibitory role in propelling hearts towards failure. Thus, the present invention is directed to characterizing the role apoptosis plays in heart failure and identification of the cleavage of SRF by caspases in failing hearts. The present inventors observed SRF cleavage by caspase 3 in human failing hearts, but none in normal hearts. One of the stably accumulated SRF fragments acted as a dominant negative transcription factor that blocked muscle specific gene activation. Tissues obtained from transplant patients who had been maintained on a left ventricular assist device (LVAD) as a bridge until transplant had reduced SRF fragmentation, not significantly different from controls. In specific embodiments of the present invention, generation of dominant negative SRF is responsible for the suppression of cardiac specific gene transcription seen in severe heart failure, and in further specific embodiments caspase 3 activation is reversible with ventricular unloading.

In one embodiment of the present invention, there is an antibody to at least a portion of a SRF polypeptide. In specific embodiments, the antibody is to an N-terminal or C-terminal portion of a SRF polypeptide. In further specific embodiments, the antibody is to at least a portion of the peptide sequence encoded in the first exon. In additional specific embodiments, the antibody is to SEQ ID NO:5, which comprises GANGGRVPGNGA.

In one embodiment of the present invention, there is a method of treating heart failure in an individual comprising preventing cleavage of serum response factor (SRF) in at least one cardiac cell of the individual. The method may be further defined as administering a therapeutically effective amount of a caspase inhibitor in a pharmaceutically acceptable composition. In specific embodiments, the caspase inhibitor is insulin-like growth factor, growth hormone, Akt, growth hormone releasing hormone, baculovirus p35, cowpox virus CrmA, Flip, acetyl-DEVD-aldehyde, or a mixture thereof.

In another embodiment of the present invention, there is a method of treating heart failure in an individual, comprising administering to the individual a therapeutically effective amount of an uncleavable SRF.

In an additional embodiment of the present invention, there is a method of diagnosing cardiac disease in an individual, comprising the step of identifying cleavage of SRF in at least one cell from a sample from said individual. The sample may be from a tissue of the individual, such as cardiac tissue, for example. The cardiac tissue may be ventricular tissue, for example. In specific embodiments, the identifying step is further defined as obtaining a sample from an individual suspected of having cardiac failure; and comparing levels of cleaved SRF in said sample with a known control reflective of levels of cleaved SRF in non-failing cardiac tissue, wherein when said sample comprises elevated levels of cleaved SRF compared to said control, said individual suspected of having cardiac failure has a positive diagnosis for cardiac failure. In a specific embodiment, the identifying step comprises immunoblot analysis for said cleaved SRF. In a further specific embodiment, the immunoblot analysis comprises an antibody against a region of SRF, such as an N-terminal region or a C-terminal region. In a specific embodiment, the N-terminal region comprises at least a portion of amino acid sequence encoded by the first coding exon of a SRF polynucleotide. The N-terminal region may comprise SEQ ID NO:5, in specific embodiments. In a particular embodiment, the cardiac disease is further defined as cardiac failure.

In another embodiment of the present invention, there is polyclonal antiserum, antibodies of which bind immunologically to a polypeptide comprising an N-terminal region of serum response factor. The serum response factor polypeptide may comprise SEQ ID NO:5. In a particular embodiment, the antibodies of said antiserum are bound to a support.

In an additional embodiment of the present invention, there is a method of treating cardiac disease in an individual, wherein the disease is associated with cleavage of SRF in at least one cell of the individual, comprising the step of administering to the individual a therapeutically effective amount of a pharmaceutically acceptable composition comprising a caspase inhibitor. The caspase being inhibited may be caspase 3, caspase 7, or both. Also, the administering step may be further defined as administering a caspase inhibitor to the individual, wherein the caspase inhibitor inhibits cleavage of serum response factor (SRF). Examples of caspase inhibitors include insulin-like growth factor, growth hormone, Akt, growth hormone releasing hormone, baculovirus p35, cowpox virus CrmA, Flip, acetyl-DEVD-aldehyde, or a mixture thereof.

In a specific embodiment, a treatment method, for example, further comprises an additional therapy, such as drug therapy, device therapy, gene therapy, nutritional and/or exercise therapy, or a combination thereof. The device therapy may comprise administration of a left ventricular assist device to the individual, in some embodiments.

In another embodiment, there is a method of treating cardiac disease in an individual, wherein the disease is associated with cleavage of SRF, comprising the step of administering to the individual a therapeutically effective amount of a pharmaceutically acceptable composition comprising an anti-apoptotic composition. The anti-apoptotic composition may be phorbol myristate acetate, in exemplary embodiments.

In an additional embodiment, there may be a method of treating cardiac disease in an individual, comprising inhibiting activity of a dominant negative form of SRF in at least one cell of the individual, such as, for example, one comprising a fragment of SRF resulting from proteolytic cleavage of SRF. The proteolytic cleavage may be from a caspase, such as caspase 3 or caspase 7.

In another embodiment of the present invention, there is a method of treating cardiac disease in an individual, wherein the disease is associated with cleavage of SRF, comprising the step of administering to the individual a therapeutically effective amount of a pharmaceutically acceptable composition comprising growth hormone releasing hormone. The cleavage of SRF results in apoptosis, in some embodiments.

In one embodiment of the present invention, there is a method of preventing cardiac disease in an individual, comprising inhibiting cleavage of serum response factor in a cardiac tissue of the individual.

In an additional embodiment of the present invention, there is a method of preventing cardiac disease in an individual, comprising inhibiting activity of a dominant negative form of SRF.

In another embodiment of the present invention, there is a kit for the treatment of cardiac failure in an individual comprising elevated levels of cleaved SRF, comprising a caspase inhibitor, an uncleavable SRF, or a combination thereof.

In an additional embodiment of the present invention, there is a method of treating heart failure in an individual, comprising the steps of providing the individual, wherein said heart failure in the individual is the direct or indirect result of cleavage of SRF in at least one cardiac cell of the individual; and administering to the individual a therapeutically effective amount of a SRF inhibitor.

In some embodiments, there is a method of treating heart failure in an individual, comprising the steps of providing the individual, wherein said heart failure in the individual is the direct or indirect result of cleavage of SRF in at least one cardiac cell of the individual; and administering to the individual a therapeutically effective amount of a SRF inhibitor, a caspase inhibitor, or both.

In other embodiments, there is a method of preventing or delaying apoptosis of a cell, comprising the step of inhibiting SRF in said cell, wherein said inhibiting is further defined as inhibiting activity of SRF in said cell; inhibiting expression of SRF in said cell; inhibiting cleavage of SRF in said cell; or a combination thereof. In a specific embodiment, the cleavage is by a caspase.

In an additional embodiment of the present invention, there is a method of treating heart disease in an individual, comprising providing the individual, said heart disease the direct or indirect result of cleavage of SRF in at least one cardiac cell of the individual; and preventing and/or inhibiting cleavage of SRF. The preventing and/or inhibiting cleavage of SRF may comprise the step of administering to the individual a therapeutically effective amount of a SRF inhibitor.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 1A shows a representative Western blot. Each lane represents a single human sample from 2 normal and 9 heart failure patients, 5 of which were on LVAD support. Proteins from myocardial tissue homogenates were analyzed by immunoblotting with anti-SRF-C antibody. FIG. 1B shows that a densitometry analysis of small fragment (32 kDa) from 13 heart failure patients and 10 LVAD support patients were made based on these Western blots and demonstrated a*p<0.05 in comparison to 7 normal heart samples. HR: heart. FIG. 1C demonstrates that active caspase 3 (20 kDa) level was increased in human failing hearts and returned to normal level after LVAD support. Proteins from myocardial tissue homogenates were analyzed by immunoblotting with an anti-caspase 3 antibody, which reacts with both precursor and active subunits.

FIG. 1A shows a schematic presentation of three cleavage sites, Aspartate (D) 82, 254 and Asp425, and their correspondent SRF fragments, 55 kDa and 32 kDa, derived from cleavage by activated caspase 3. FIG. 1B shows that SRF-N, SRF-C and full length SRF were expressed in transfected CV1 cells. The cell lysates were analyzed by Western blot; only SRF-N fragment and full length SRF were detected by anti-SRF-N. The same membrane was blotted by anti-SRF-C antibody and SRF-C and full length of SRF were recognized, indicating the specificities of the antibodies (NS abbreviated for non-specific). FIG. 1C demonstrates that the SRF fragments (55 and 32 kDa) accumulated in human failing hearts was recognized by both anti-SRF-N and anti-SRF-C antibodies, suggesting a combination of both N- and C-terminal domain fragments per fragment size, as schematized in panel A.

FIG. 4A is SRF-N repressed cardiac α-actin promoter in neonatal rat cardiomyocytes. Cultured neonatal cardiomyocytes were transfected with αCA-luc reporter plasmid together with either the control vector plasmid or expression plasmid encoding SRF or SRF-N. FIG. 1B shows SRF-N repressed skeletal α-actin promoter in C2C12 myoblasts. Cells were transfected with SK-luc reporter plasmid together with either the control vector plasmid or expression plasmid encoding SRF or SRF-N. All data were pooled from three repeated experiments. FIG. 1C provides immunofluorescence analysis for SRF-N and SRF showing the expression and capability of dominant negative SRF-N to localize to myogenic nuclei, as well as full length SRF in transfected cardiac myocytes. FIG. 4D provides EMSAs with bacterial expressed SRF and in vitro caspase 3 clipped SRF-N that were performed as previously described (Chen and Schwartz, 1996) and demonstrated that SRF-N retains DNA binding activity.

DETAILED DESCRIPTION OF THE INVENTION

I. Definitions

Figure 1:
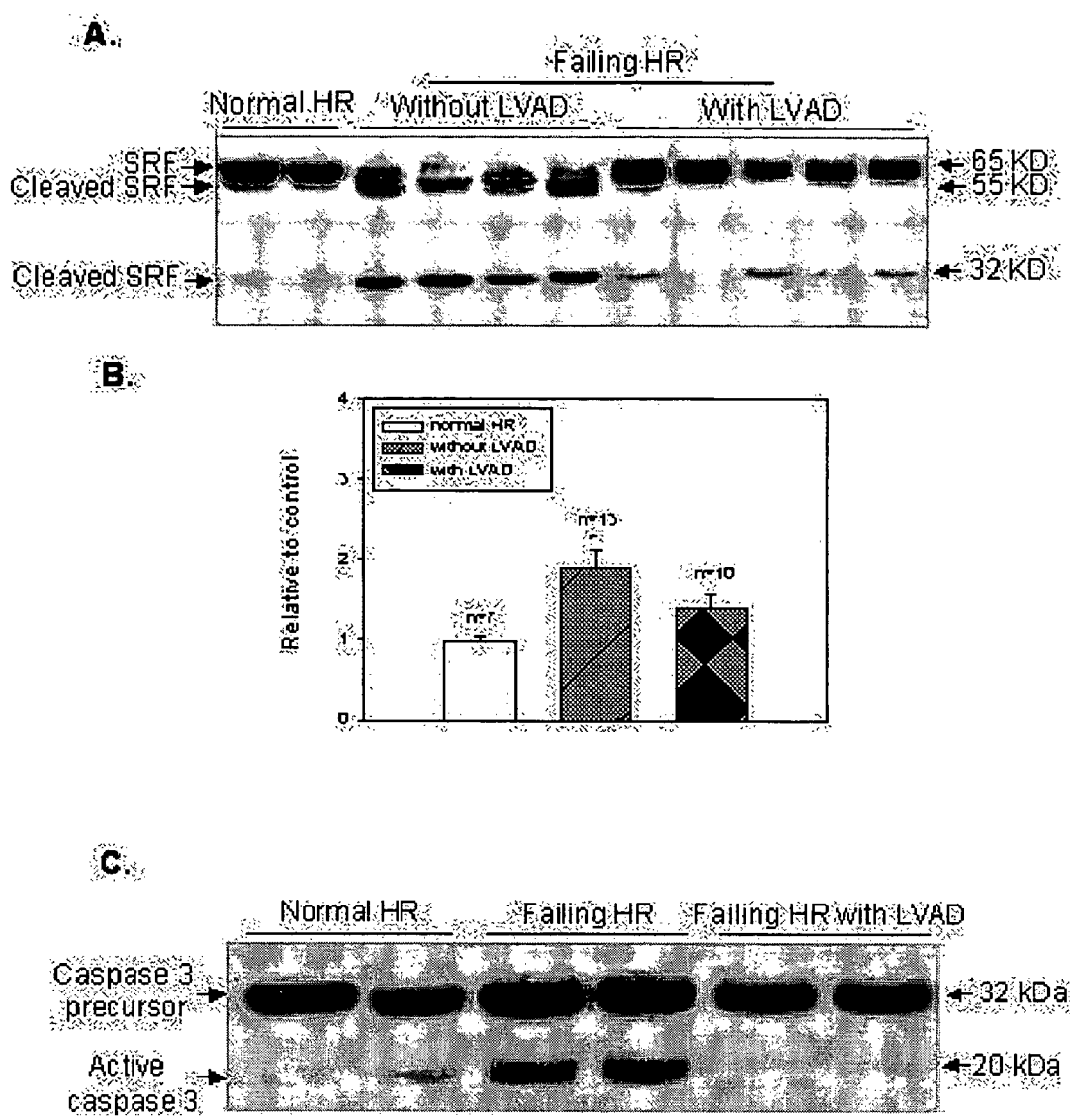
FIGS. 1A through 1C demonstrate that full length SRF was markedly reduced in human failing hearts accompanied by the accumulation of two major SRF subspecies of 55 and 32 kDa that were attenuated with LVAD support.

The term "a" or "an" as used herein in the specification may mean one or more. As used herein in the claim(s), when used in conjunction with the word "comprising", the words "a" or "an" may mean one or more than one. As used herein "another" may mean at least a second or more.

As used herein, the term "cardiac failure" refers to a clinical syndrome in which heart disease comprises reduction in cardiac output, increase in venous pressures, and is accompanied by molecular abnormalities that cause progressive deterioration of the failing heart and premature myocardial cell death.

The terms "cardiovascular disease" or "cardiac disease" as used herein is defined as a medical condition related to the cardiovascular (heart) or circulatory system (blood vessels). Cardiovascular disease includes, but is not limited to, diseases and/or disorders of the pericardium (i.e., pericardium), heart valves (i.e., incompetent valves, stenosed valves, rheumatic heart disease, mitral valve prolapse, aortic regurgitation), myocardium (coronary artery disease, myocardial infarction, heart failure, ischemic heart disease, angina) blood vessels (i.e., arteriosclerosis, aneurysm) or veins (i.e., varicose veins, hemorrhoids). Yet further, one skill in the art recognizes that cardiovascular diseases can result from congenital defects, genetic defects, environmental influences (i.e., dietary influences, lifestyle, stress, etc.), and other defects or influences, and combinations thereof. In a specific embodiment, cardiac disease comprises failure of the heart.

The term "cardiovascular tissue" as used herein is defined as heart tissue and/or blood vessel tissue.

As used herein, the term "coronary artery disease" (CAD) refers to a type of cardiovascular disease. CAD is caused by gradual blockage of the coronary arteries. One of skill in the art realizes that in coronary artery disease, atherosclerosis (commonly referred to as "hardening of the arteries") causes thick patches of fatty tissue to form on the inside of the walls of the coronary arteries. These patches are called plaque. As the plaque thickens, the artery narrows and blood flow decreases, which results in a decrease in oxygen to the myocardium. This decrease in blood flow precipitates a series of consequences for the myocardium. For example, interruption in blood flow to the myocardium results in an "infarct" (myocardial infarction), which is commonly known as a heart attack.

As used herein, the term "damaged myocardium" refers to myocardial cells that have been exposed to ischemic conditions. These ischemic conditions may be caused by a myocardial infarction, or other cardiovascular disease or related complaint. The lack of oxygen causes the death of the cells in the surrounding area, leaving an infarct, which eventually scars.

As used herein, the term "infarct" or "myocardial infarction (MI)" refers to an interruption in blood flow to the myocardium. Thus, one of skill in the art refers to MI as death of cardiac muscle cells resulting from inadequate blood supply.

As used herein, the term "ischemic heart disease" refers to a lack of oxygen due to inadequate perfusion or blood supply. Ischemic heart disease is a condition having diverse etiologies. One specific etiology of ischemic heart disease is the consequence of atherosclerosis of the coronary arteries.

As used herein, the term "myocardium" refers to the muscle of the heart.

As used herein, the term "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The term "therapeutically effective amount" as used herein refers to an amount that results in an improvement or remediation of the disease, disorder, or symptoms of the disease or condition.

The term "treating" and "treatment" as used herein refers to administering to a subject a therapeutically effective amount of a the composition so that the subject has an improvement in the disease. The improvement is any improvement or remediation of the symptoms. The improvement is an observable or measurable improvement. Thus, one of skill in the art realizes that a treatment may improve the disease condition, but may not be a complete cure for the disease.

The term "uncleavable SRF" as used herein refers to a serum response factor having the caspase-cleavable sites mutated so that they can not be cleaved. In a specific embodiment, the uncleavable SRF is resistant to cleavage by a caspase. In other specific embodiments, the uncleavable SRF is resistant to cleavage by any protease, such as any aspartate protease, such as any cysteine-dependent aspartate protease. In further specific embodiments, the uncleavable SRF comprises mutated sites at Asp 245 and Asp 254.

II. The Present Invention

Human heart failure is the leading cause of combined morbidity and mortality in the United States and other developed industrial nations. It remains an incurable disease process with an estimated five-year mortality of 30-50% for the patients with advanced disease. Although great advances have been made in the treatment for failing heart, the understanding of the molecular mechanism leading to heart failure is still limited.

Recent studies have found the occurrence of apoptosis in failing heart. The loss of functional myocytes via cell apoptosis pathway appears to play an important role in the progression of cardiac failure (Kang and Izumo, 2000; Haunstetter and Izumo, 1998; Hirota et al., 1999). The present inventors have made the surprising observation that the amount of cleaved SRF by caspases was significantly increased in human failing heart tissues compared to normal hearts. The depletion of SRF by caspases in specific embodiments leads to down-regulation of cardiac specific gene programs. In additional embodiments, the cleaved SRF fragments act as dominant negatives for the uncleaved SRF and ultimately shut down the important contractile protein synthesis, driving the heart into failure.

The present invention specifically demonstrates that modest caspase 3 activation in heart failure sequentially cleaved SRF and generated a dominant negative transcription factor, which, in specific embodiments, leads to the depression of transcription of cardiac-specific genes. Moreover, the data indicate that, in specific embodiments, caspase 3 activation is reversible in the failing heart with ventricular unloading.

Specifically, ventricular muscle samples from patients with end stage heart failure during heart transplants was obtained and analyzed by western blot using two anti-SRF antibodies raised against N-terminal and C-terminal amino acids of human SRF, respectively. The amount of cleaved SRF by caspases was significantly increased in all forms of human failing heart tissues compared to normal hearts. The depletion of SRF by caspases in specific embodiments leads to downregulation of cardiac-specific gene programs. The accumulation of caspase-cleaved SRF fragments, in specific embodiments, acting as dominant negatives for the uncleaved SRF ultimately shut down the important contractile protein synthesis, driving the heart into failure.

More specifically, protein samples from left ventricular cardiac tissues, from 13 patients with end-stage heart failure and 7 normal hearts, were analyzed with SRF antibodies. SRF (65 kDa) was markedly reduced and processed into 55 kDa and 32 kDa subfragments, in all failing hearts. SRF was intact in normal samples. Specific antibodies to N-terminal and C-terminal SRF sequences revealed 3 alternative caspase 3 cleavage sites, so that two fragments were detected of each size (55 kDa and/or 32 kDa) containing either the N- or C-terminal SRF sequence. Expression of SRF-N, the 32 kDa fragment, in myogenic cells inhibited the transcriptional activity of α-actin gene promoters by 50-60%. Thus, SRF-N functioned as a dominant negative transcription factor. SRF fragmentation was reduced in samples taken at the time of transplant from 10 patients maintained on Left Ventricular Assist Devices (LVAD) until transplant.

III. Treatment of Cardiovascular/Cardiac Disease

Cardiovascular/cardiac diseases and/or disorders include, but are not limited to, diseases and/or disorders of the pericardium (i.e., pericardium), heart valves (i.e., incompetent valves, stenosed valves, Rheumatic heart disease, mitral valve prolapse, aortic regurgitation), myocardium (coronary artery disease, myocardial infarction, heart failure, ischemic heart disease, angina) blood vessels (i.e., arteriosclerosis, aneurysm) or veins (i.e., varicose veins, hemorrhoids). In specific embodiments, the cardiovascular disease includes, but is not limited to, coronary artery diseases (i.e., arteriosclerosis, atherosclerosis, and other diseases of the arteries, arterioles and capillaries or related complaint), myocardial infarction and ischemic heart disease.

Accordingly, the invention involves the treatment of cardiovascular/cardiac disease and/or heart failure by preventing cleavage of SRF, inhibiting cleavage of SRF, reversing cleavage of SRF, ameliorating cleavage of SRF, or a combination thereof. In specific embodiments, the invention comprises administration of caspase inhibitor(s), such as insulin-like growth factor, growth hormone, Akt, growth hormone releasing hormone, baculovirus p35, cowpox virus CrmA, Flip, acetyl-DEVD-aldehyde, or any caspase inhibitor that inhibits cleavage of SRF of any kind and/or for administering and/or uncleavable SRF. It is envisioned that one of skill in the art will know the most advantageous routes of administration depending upon the disease. In specific embodiments, it is contemplated that the caspase inhibitor(s) and/or uncleavable SRF or pharmaceutical composition comprising same can be administered via injection, which includes, but is not limited to subcutaneous, intravenous, intraarterial, intramuscular, intraperitoneal, intramyocaridal, transendocardial, transepicardial, intranasal and intrathecal.

Yet further, it is envisioned that the caspase inhibitor(s) and/or uncleavable SRF or pharmaceutical composition of the present invention can be administered to the subject in an injectable formulation containing any compatible carrier, such as various vehicles, adjuvants, additives, and diluents. Yet further, the caspase inhibitor(s) and/or uncleavable SRF or pharmaceutical composition can be administered parenterally to the subject in the form of slow-release subcutaneous implants or targeted delivery systems such as monoclonal antibodies, iontophoretic, polymer matrices, liposomes, and microspheres.

Treatment regimens may vary as well, and often depend on the cardiovascular disease or disorder, disease progression, and health and age of the subject. Obviously, certain types of cardiovascular disease will require more aggressive treatment, while at the same time, certain patients cannot tolerate more taxing protocols. The clinician will be best suited to make such decisions based on the known efficacy and toxicity (if any) of the therapeutic formulations.

Suitable regimes for initial administration and further doses or for sequential administrations also are variable, and may include an initial administration followed by subsequent administrations; but nonetheless, may be ascertained by the clinician.

For example, the caspase inhibitor(s) and/or uncleavable SRF or the pharmaceutical composition thereof can be administered initially, and thereafter maintained by further administration. For instance, a composition of the invention can be administered in one type of composition and thereafter further administered in a different or the same type of composition. For example, a composition of the invention can be administered by intravenous injection to bring blood levels to a suitable level. The subject's levels are then maintained by a subcutaneous implant form, although other forms of administration, dependent upon the subject's condition, can be used.

As used herein the term "effective amount" is defined as an amount of the caspase inhibitor(s) and/or uncleavable SRF or pharmaceutical composition thereof that will repair damaged myocardium, prevent further injury to heart tissue, regenerate cardiomyocytes, regenerate vascular cells, provide structural stability to an injured myocardium or provide at least partially restored functionality to an injured myocardium. Thus, an effective amount is an amount sufficient to detectably and repeatedly ameliorate, reduce, minimize or limit the extent of the disease or its symptoms.

The precise determination of what would be considered an effective dose may be based on factors individual to each subject, including their size, age, size of the infarct, and amount of time since damage. Therefore, dosages can be readily ascertained by those skilled in the art from this disclosure and the knowledge in the art. Thus, the skilled artisan can readily determine the amount of compound and optional additives, vehicles, and/or carrier in compositions and to be administered in methods of the invention. Of course, for any composition to be administered to an animal or human, and for any particular method of administration, it is preferred to determine the toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. Furthermore, the time for sequential administrations can be ascertained without undue experimentation.

The treatments may include various "unit doses." Unit dose is defined as containing a predetermined-quantity of the therapeutic composition. The quantity to be administered, and the particular route and formulation, are within the skill of those in the clinical arts. A unit dose need not be administered as a single injection but may comprise continuous infusion over a set period of time.

In further embodiments, the caspase inhibitor(s) and/or uncleavable SRF are administered to a subject suffering from myocardial infarction. It is contemplated that the caspase inhibitor(s) and/or uncleavable SRF can alleviate the symptoms associated with myocardial infarction. For example, the caspase inhibitor(s) and/or uncleavable SRF migrates to the infarcted myocardium and results in repair or regeneration of the infarcted myocardium.

Further embodiments of the present invention involve a method of targeting injured myocardium by delivering to a subject the caspase inhibitor(s) and/or uncleavable SRF, as described herein, wherein the caspase inhibitor(s) migrate or hone and attach to the injured myocardium. The caspase inhibitor(s) and/or uncleavable SRF may be administered intravenously to the subject. Thus, the caspase inhibitor(s) and/or uncleavable SRF maneuvers the systemic circulation and migrates or targets or homes to the damaged or injured myocardium. Once the caspase inhibitor(s) and/or uncleavable SRF have migrated to the damaged myocardium, the caspase inhibitor(s) and/or uncleavable SRF repairs the damage myocardium and/or prevents further damage to the myocardium.

Yet further, it is also contemplated that a caspase inhibitor and/or uncleavable SRF useful for cardiac development is useful in the present invention. The caspase inhibitor and/or uncleavable SRF can be administered via an expression vector that expresses is. Development of expression vectors are well known and used in the art, for example Manniatis et al. (1982). Once the expression vector is generated, it can be delivered to cardiac cells via standard transfection protocols, which are well-known and used in the art. These standard transfection protocols include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu and Wu, 1987; Wu and Wu, 1988).

Yet further, it is envisioned that cardiac cells are obtained from an autologous source, uncleavable SRF or caspase inhibitor(s) are delivered to the cells, and the cells are administered to cardiac tissue. The autologous source can be tissue that is obtained from a tissue biopsy. The cells are proliferated in vitro to generate an abundance of the autologous cells.

After a suitable number of cells have been proliferated, the uncleavable SRF or caspase inhibitor(s) are introduced to the autologous cells and are administered to the subject, such as via an intravenous injection. In other embodiments the autologous source cells comprising uncleavable SRF and/or caspase inhibitor(s) are administered to an individual as a tissue, such as a cardiac tissue, including a vessel.

IV. Combined Cardiac Disease Treatments

In order to increase the effectiveness of the compositions and/or methods described herein, it may be desirable to combine these compositions and methods of the invention with a known agent effective in the treatment of cardiac disease or disorder. In some embodiments, it is contemplated that a conventional therapy or agent, including but not limited to, a pharmacological therapeutic agent, a surgical therapeutic agent (e.g., a surgical procedure), a device, or a combination thereof, may be combined with the caspase inhibitor(s) and/or uncleavable SRF of the present invention or a tissue derived therefrom. In a non-limiting example, a therapeutic benefit comprises repair of myocardium or vascular tissue or reduced restenosis following vascular or cardiovascular intervention, such as occurs during a medical or surgical procedure.

This process may involve contacting the cell(s) with an agent(s) and the caspase inhibitor(s) and/or uncleavable SRF of the present invention at substantially the same time or within a period of time wherein separate administration of the caspase inhibitor(s) and/or uncleavable SRF and an agent to a cell, tissue or organism produces a desired therapeutic benefit. The terms "contacted" and "exposed," when applied to a cell, tissue or organism, are used herein to describe the process by which the caspase inhibitor(s) and/or uncleavable SRF and/or therapeutic agent(s) are delivered to a target cell, tissue or organism or are placed in direct juxtaposition with the target cell, tissue or organism. The cell, tissue or organism may be contacted (e.g., by administration) with a single composition or pharmacological formulation that comprises both a caspase inhibitor(s) and/or uncleavable SRF and one or more agents, or by contacting the cell with two or more distinct compositions or formulations, wherein one composition includes a caspase inhibitor(s) and/or uncleavable SRF and the other includes one or more agents.

The treatment may precede, be co-current with and/or follow the other agent(s) by intervals ranging from minutes to weeks. In embodiments where the caspase inhibitor(s) and/or uncleavable SRF, and other agent(s) are applied separately to a cell, tissue or organism, one would generally ensure that a significant period of time did not expire between the time of each delivery, such that the caspase inhibitor(s) and/or uncleavable SRF and agent(s) would still be able to exert an advantageously combined effect on the cell, tissue or organism. For example, in such instances, it is contemplated that one may contact the cell, tissue or organism with two, three, four or more modalities substantially simultaneously (i.e. within less than about a minute) as the caspase inhibitor(s) and/or uncleavable SRF. In other aspects, one or more agents may be administered within of from substantially simultaneously, about minutes to hours to days to weeks and any range derivable therein, prior to and/or after administering the smooth cells or a tissue derived therefrom.

Administration of the caspase inhibitor(s) and/or uncleavable SRF composition to a cell, tissue or organism may follow general protocols for the administration of vascular or cardiovascular therapeutics, taking into account the toxicity, if any. It is expected that the treatment cycles would be repeated as necessary. In particular embodiments, it is contemplated that various additional agents may be applied in any combination with the present invention.

A. Pharmacological Therapeutic Agents

Pharmacological therapeutic agents and methods of administration, dosages, etc., are well-known to those of skill in the art (see for example, the "Physicians Desk Reference", Goodman & Gilman's "The Pharmacological Basis of Therapeutics", "Remington's Pharmaceutical Sciences", and "The Merck Index, Eleventh Edition", incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

Non-limiting examples of a pharmacological therapeutic agent that may be used in the present invention include an antihyperlipoproteinemic agent, an antiarteriosclerotic agent, an antithrombotic/fibrinolytic agent, a blood coagulant, an antiarrhythmic agent, an antihypertensive agent, a vasopressor, a treatment agent for congestive heart failure, or a combination thereof.

B. Surgical Therapeutic Agents

In certain aspects, a therapeutic agent may comprise a surgery of some type, which includes, for example, preventative, diagnostic or staging curative and/or palliative surgery. Surgery, and in particular, a curative surgery, may be used in conjunction with other therapies, such as the present invention and one or more other agents.

Such surgical therapeutic agents for vascular and cardiovascular diseases and disorders are well known to those of skill in the art, and may comprise, but are not limited to, performing surgery on an organism, providing a cardiovascular mechanical prostheses, angioplasty, coronary artery reperfusion, catheter ablation, providing an implantable cardioverter defibrillator to the subject, mechanical circulatory support or a combination thereof. Non-limiting examples of a mechanical circulatory support that may be used in the present invention comprise an intra-aortic balloon counterpulsation, left ventricular assist device or combination thereof.

Further treatment of the area of surgery may be accomplished by perfusion, direct injection, systemic injection or local application of the area with at least one additional therapeutic agent (e.g., a caspase inhibitor(s) and/or uncleavable SRF, a pharmacological therapeutic agent, and so forth), as would be known to one of skill in the art or described herein.

V. Kits

Any of the compositions described herein may be comprised in a kit. In a non-limiting example, the stem cells, lipid, and/or additional agent, may be comprised in a kit. The kits will thus comprise, in suitable container means, the stem cells and a lipid, and/or an additional agent of the present invention. In specific embodiments, the kit comprises a caspase inhibitor(s) and/or uncleavable SRF.

The kits may comprise a suitably aliquoted caspase inhibitor(s) and/or uncleavable SRF and/or additional agent compositions of the present invention, whether labeled or unlabeled, as may be used to prepare a standard curve for a detection assay. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the stem cells or the pharmacological composition of the present invention, lipid, additional agent, and any other reagent containers in close confinement for commercial sale. Such containers may include injection or blow-molded plastic containers into which the desired vials are retained.

Therapeutic kits of the present invention are kits comprising the caspase inhibitor(s) and/or uncleavable SRF. Such kits will generally contain, in suitable container means, a pharmaceutically acceptable formulation of the caspase inhibitor(s) and/or uncleavable SRF. The kit may have a single container means, and/or it may have distinct container means for each compound.

When the components of the kit are provided in one and/or more liquid solutions, the liquid solution is an aqueous solution, with a sterile aqueous solution being particularly preferred. The stem cell compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the stem cells are placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Irrespective of the number and/or type of containers, the kits of the invention may also comprise, and/or be packaged with, an instrument for assisting with the injection/administration and/or placement of the ultimate the stem cell composition within the body of an animal. Such an instrument may be a syringe, pipette, forceps, and/or any such medically approved delivery vehicle.

VI. Definitions and Techniques Affecting Gene Products and Genes

C. SRF Gene Products and Genes

In this patent, the terms "SRF gene product" and "SRF" refer to proteins and polypeptides having amino acid sequences that are substantially identical to the native SRF amino acid sequences (or RNA, if applicable) or that are biologically active, in that they are capable of performing functional activities similar to an endogenous SRF and/or cross-reacting with anti-SRF antibody raised against SRF. In analogous embodiments, "SRF gene product," and "SRF" are referred to herein.

In a specific embodiment, a function of SRF is to be involved in protein-protein interactions, and other embodiments include associating with adhesion plaques and filamentous actin, interact with α-actinin, interact with zyxin, regulate the stability and structure of adhesion complexes, and a combination thereof. In other specific embodiments, SRF functions to integrate intracellular signals, assist as a docking surface for cofactor binding, and influence gene expression. In preferred embodiments, a SRF gene product is an uncleavable SRF incapable of cleavage by a caspase or other similar enzyme.

An example of a SRF polypeptide sequence, followed by its National Center for Biotechnology's GenBank database Accession No. includes a SRF polypeptide comprising SEQ ID NO:2 (NP_003122), or a functionally similar fragment thereof.

The term "SRF gene product" includes analogs of the respective molecules that exhibit at least some biological activity in common with their native counterparts. Such analogs include, but are not limited to, truncated polypeptides and polypeptides having fewer amino acids than the native polypeptide. Furthermore, those skilled in the art of mutagenesis will appreciate that homologs to the mouse SRF polynucleotide, including human homologs, which homologs are as yet undisclosed or undiscovered, may be used in the methods and compositions disclosed herein.

The term "SRF gene" "SRF polynucleotide" or "SRF nucleic acid" refers to any DNA sequence that is substantially identical to a DNA sequence encoding an SRF gene product as defined above. The term also refers to RNA or antisense sequences compatible with such DNA sequences. An "SRF gene or SRF polynucleotide" may also comprise any combination of associated control sequences. In a specific embodiment of the present invention, a SRF polynucleotide of SEQ ID NO:3 (NM_003131) or a functionally similar fragment thereof, is utilized.

Thus, nucleic acid compositions encoding SRF are herein provided and are also available to a skilled artisan at accessible databases, including the National Center for Biotechnology Information's GenBank database and/or commercially available databases, such as from Celera Genomics, Inc. (Rockville, Md.). Also included are splice variants that encode different forms of the protein, if applicable. The nucleic acid sequences may be naturally occurring or synthetic.

As used herein, the terms "SRF nucleic acid sequence," "SRF polynucleotide," and "SRF gene" refer to nucleic acids provided herein, homologs thereof, and sequences having substantial similarity and function, respectively. A skilled artisan recognizes that the sequences are within the scope of the present invention if they encode a product which, facilitates diagnosis of cardiac failure and/or provides cardiac disease therapy, and furthermore knows how to obtain such sequences, as is standard in the art.

The term "substantially identical", when used to define either a SRF amino acid sequence or SRF polynucleotide sequence, means that a particular subject sequence, for example, a mutant sequence, varies from the sequence of natural SRF by one or more substitutions, deletions, or additions, the net effect of which is to retain at least some biological activity of the SRF protein, respectively. Alternatively, DNA analog sequences are "substantially identical" to specific DNA sequences disclosed herein if: (a) the DNA analog sequence is derived from coding regions of the natural SRF gene; or (b) the DNA analog sequence is capable of hybridization of DNA sequences of (a) under moderately stringent conditions and which encode biologically active SRF; or (c) DNA sequences which are degenerative as a result of the genetic code to the DNA analog sequences defined in (a) or (b). Substantially identical analog proteins will be greater than about 80% similar to the corresponding sequence of the native protein. Sequences having lesser degrees of similarity but comparable biological activity are considered to be equivalents. In determining polynucleotide sequences, all subject polynucleotide sequences capable of encoding substantially similar amino acid sequences are considered to be substantially similar to a reference polynucleotide sequence, regardless of differences in codon sequence.

1. Percent Similarity

Percent similarity may be determined, for example, by comparing sequence information using the GAP computer program, available from the University of Wisconsin Geneticist Computer Group. The GAP program utilizes the alignment method of Needleman et al., 1970, as revised by Smith et al., 1981. Briefly, the GAP program defines similarity as the number of aligned symbols (i.e. nucleotides or amino acids) which are similar, divided by the total number of symbols in the shorter of the two sequences. The preferred default parameters for the GAP program include (1) a unitary comparison matrix (containing a value of 1 for identities and 0 for non-identities) of nucleotides and the weighted comparison matrix of Gribskov et al., 1986, (2) a penalty of 3.0 for each gap and an additional 0.01 penalty for each symbol and each gap; and (3) no penalty for end gaps.

2. Polynucleotide Sequences

In certain embodiments, the invention concerns the use of SRF genes and gene products, such as the SRF that includes a sequence which is essentially that of the known SRF gene, or the corresponding protein, respectively. The term "a sequence essentially as SRF" means that the sequence substantially corresponds to a portion of the SRF gene, respectively, and has relatively few bases or amino acids (whether DNA or protein) that are not identical to those of SRF (or a biologically functional equivalent thereof, when referring to proteins), respectively. The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids which are identical or functionally equivalent to the amino acids of SRF will be sequences which are "essentially the same".

SRF genes that have functionally equivalent codons, respectively, are also covered by the invention. The term "functionally equivalent codon" is used herein to refer to codons that encode the same amino acid, such as the six codons for arginine or serine, and also refers to codons that encode biologically equivalent amino acids (Table 1).

TABLE 1

FUNCTIONALLY EQUIVALENT CODONS.

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic Acid | Asp | D | GAC | GAU | | | | |
| Glutamic Acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |

TABLE 1-continued

FUNCTIONALLY EQUIVALENT CODONS.

| Amino Acids | | | Codons | | | | | |
|---|---|---|---|---|---|---|---|---|
| Asparagine | Asn | N | AAC | AAU | | | | |
| Proline | Pro | P | CCA | CCC | CCU | | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

It will also be understood that amino acid and polynucleotide sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to polynucleotide sequences which may, for example, include various non-coding sequences flanking either of the 5' or 3' portions of the coding region or may include various internal sequences, i.e., introns, which are known to occur within genes.

In certain embodiments, the invention concerns the use of uncleavable SRF polynucleotide sequences, truncated SRF polynucleotide sequences or polynucleotide sequences that encode a SRF polypeptide, respectively, with less amino acids than native SRF. The present invention also encompasses the use of DNA segments that are complementary, or essentially complementary, to the sequences set forth in the specification. Polynucleotide sequences that are "complementary" are those which are capable of base-pairing according to the standard Watson-Crick complementarily rules. As used herein, the term "complementary sequences" means polynucleotide sequences which are substantially complementary, as may be assessed by the same nucleotide comparison set forth above, or as defined as being capable of hybridizing to the polynucleotide segment in question under relatively stringent conditions such as those described herein.

3. Biologically Functional Equivalents

As mentioned above, modification and changes may be made in the structure of SRF and still obtain a molecule having like or otherwise desirable characteristics, respectively. For example, certain amino acids may be substituted for other amino acids in a protein structure without appreciable loss of activity for upregulating expression of smooth muscle-specific polynucleotides. Since it is the interactive capacity and nature of a protein that defines that protein's biological functional activity, certain amino acid sequence substitutions and/or deletions can be made in a protein sequence (or, of course, its underlying DNA coding sequence) and nevertheless obtain a protein with like or even countervailing properties (e.g., antagonistic v. agonistic). It is thus contemplated by the inventors that various changes may be made in the sequence of the SRF proteins or peptides (or underlying DNA) without appreciable loss of their biological utility or activity, respectively. Included in such changes are truncated SRF polypeptides and SRF polypeptides having less amino acid residues than native SRF.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Of course, a plurality of distinct proteins/peptides with different substitutions may easily be made and used in accordance with the invention.

It is also well understood that where certain residues are shown to be particularly important to the biological or structural properties of a protein or peptide, e.g., residues in active sites, such residues may not generally be exchanged. This is the case in the present invention, where any changes in SRF that render the respective polypeptide incapable of preventing or delaying entry into mitosis following DNA damage would result in a loss of utility of the resulting peptide for the present invention.

Amino acid substitutions, such as those that might be employed in modifying SRF are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte and Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

4. Sequence Modification Techniques

Modifications to the SRF peptides may be carried out using techniques such as site-directed mutagenesis. Such modifications may comprise those directed to producing an uncleavable SRF. In specific embodiments, an uncleavable SRF is defined as one lacking cleavability at least at $Asp^{245}$ and/or $Asp^{254}$. Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications (Adelman et al., 1983). As will be appreciated, the technique typically employs a phage vector that exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which includes within its sequence a DNA sequence which encodes at least the SRF gene. An oligonucleotide primer bearing the desired mutated sequence is prepared, generally synthetically, for example by the method of Crea et al. (1978). This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original nonmutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful SRF and is not meant to be limiting as there are other ways in which sequence variants of these peptides may be obtained. For example, recombinant vectors encoding the desired genes may be treated with mutagenic agents to obtain sequence variants (see, e.g., a method described by Eichenlaub, 1979) for the mutagenesis of plasmid DNA using hydroxylamine.

5. Antisense Constructs

In some cases, a gene is essential to the life of the cell, wherein its removal, such as by homologous replacement, results in the death of the cell. In other cases, a gene may have aberrant functions that cannot be overcome by replacement gene therapy, even where the "wild-type" molecule is expressed in amounts in excess of the mutant polypeptide. Antisense treatments are one way of addressing these situations. Antisense technology also may be used to "knock-out" function of SRF in the development of cell lines or transgenic mice for research, diagnostic and screening purposes.

Antisense methodology takes advantage of the fact that nucleic acids tend to pair with "complementary" sequences. By complementary, it is meant that polynucleotides are those that are capable of base-pairing according to the standard Watson-Crick complementarily rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarily to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences that are completely complementary will be sequences that are entirely complementary throughout their entire length and have no base mismatches. Other sequences with lower degrees of homology also are contemplated. For example, an antisense construct that has limited regions of high homology, but also contains a non-homologous region (e.g., ribozyme) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

6. RNA Interference

RNA interference (RNAi) is the process of sequence-specific, post-transcriptional gene silencing in animals and plants, initiated by double-stranded RNA (dsRNA) that is homologous in sequence to the silenced gene. Elbashir et al. (2001a) demonstrated that 21- and 22-nt RNA fragments are the sequence-specific mediators of RNAi. In a specific embodiment, the short interfering RNAs (siRNAs) are generated by an RNase III-like processing reaction from long dsRNA. Chemically synthesized siRNA duplexes with overhanging 3' ends mediate efficient target RNA cleavage in the lysate, and the cleavage site is located near the center of the region spanned by the guiding siRNA. Furthermore, the direction of dsRNA processing determines whether sense or antisense target RNA can be cleaved by the siRNA-protein complex. Also, Elbashir et al. (2001b) showed that 21-nucleotide siRNA duplexes specifically suppress expression of endogenous and heterologous genes in different mammalian cell lines, including human embryonic kidney (293) and HeLa cells.

Therefore, a skilled artisan recognizes that 21-nucleotide siRNA duplexes provide an effective tool for studying gene function in mammalian cells and are useful as gene-specific therapeutics.

7. Synthetic Polypeptides

The present invention also describes SRF proteins and related peptides for use in various embodiments of the present invention. The SRF polypeptide may have fewer amino acids than native SRF. Relatively small peptides can be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

8. Other Structural Equivalents

In addition to the SRF peptidyl compounds described herein, the inventors also contemplate that other sterically similar compounds may be formulated to mimic the key portions of the peptide structure. Such compounds may be used in the same manner as the peptides of the invention and hence are also functional equivalents. The generation of a structural functional equivalent may be achieved by the techniques of modeling and chemical design known to those of skill in the art. It will be understood that all such sterically similar constructs fall within the scope of the present invention.

D. Expression Vectors

In certain aspects of the present invention it may be necessary to express the SRF proteins and/or polypeptides. Throughout this application, the term "expression construct" is meant to include any type of genetic construct containing a polynucleotide coding for a gene product in which part or all of the polynucleotide encoding sequence is capable of being transcribed. The transcript may be translated into a protein, but it need not be. Thus, in certain embodiments, expression includes both transcription of a SRF polynucleotide, respectively, and translation of the respective SRF mRNA into an SRF protein or polypeptide product, respectively. In other embodiments, expression only includes transcription of the polynucleotide encoding an SRF or its complement. In some embodiments, the SRF sequences are comprised on three or more separate vectors. In other embodiments, the SRF sequences are comprised on one or two vectors.

A skilled artisan recognizes that if more than one vector is utilized, it is preferential to have nonidentical means, such as markers, to monitor uptake of the vector. Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art Examples of some markers include ampicillin, neomycin, kanamycin, tetracycline, and β-galactosidase.

In order for the construct to effect expression of at least a SRF transcript, the polynucleotide encoding the SRF polynucleotide, respectively, will be under the transcriptional control of a promoter. A "promoter" refers to a DNA sequence recognized by the synthetic machinery of the host cell, or introduced synthetic machinery, that is required to initiate the specific transcription of a gene. The phrase "under transcriptional control" means that the promoter is in the correct location in relation to the polynucleotide to control RNA polymerase initiation and expression of the polynucleotide. In specific embodiments, the promoter comprises a SRE or CArG box, an example of which is provided in SEQ ID NO:1. In a specific embodiment, the promoter is SM22α promoter or SMA promoter.

In a preferred embodiment the promoter is a synthetic myogenic promoter and hGH 3' untranslated region is in the 3' untranslated region. In a specific embodiment of the present invention there is utilized a synthetic promoter, termed SPc5-12 (Li et al., 1999) (SEQ ID NO:4), which contains a proximal serum response element (SRE) from skeletal α-actin, multiple MEF-2 sites, MEF-1 sites, and TEF-1 binding sites, and greatly exceeds the transcriptional potencies of natural myogenic promoters. Other elements, including trans-acting factor binding sites and enhancers may be used in accordance with this embodiment of the invention. In an alternative embodiment, a natural myogenic promoter is utilized, and a skilled artisan is aware how to obtain such promoter sequences from databases including the National Center for Biotechnology Information (NCBI) GenBank database.

The term promoter will be used herein to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best-known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter that is employed to control the expression of a SRF polynucleotide, respectively, is not believed to be critical, so long as it is capable of expressing the polynucleotide in the targeted cell at sufficient levels. Thus, where a human cell is targeted, it is preferable to position the polynucleotide-coding region adjacent to and under the control of a promoter that is capable of being expressed in a human cell. Generally speaking, such a promoter might include either a human or viral promoter. However, in specific embodiments, the promoter is operable in fibroblasts, stem cells, smooth muscle cells, cardiomyocytes and/or a combination thereof.

In various embodiments, the human cytomegalovirus (CMV) immediate early gene promoter, the SV40 early promoter and the Rous sarcoma virus long terminal repeat can be used to obtain high-level expression of the SRF, CRP, and/or GATA polynucleotide(s). The use of other viral or mammalian cellular or bacterial phage promoters that are well-known in the art to achieve expression of polynucleotides is contemplated as well, provided that the levels of expression are sufficient to produce a growth inhibitory effect.

By employing a promoter with well-known properties, the level and pattern of expression of a polynucleotide following transfection can be optimized. For example, selection of a promoter that is active in muscle cells permits tissue-specific expression of SRF polynucleotides, respectively. Table 2 lists several elements/promoters that may be employed, in the context of the present invention, to regulate the expression of SRF constructs. This list is not intended to be exhaustive of all the possible elements involved in the promotion of SRF expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally, any promoter/enhancer combination (as per the Eukaryotic Promoter Data Base EPDB) could also be used to drive expression of a SRF construct. Use of a T3, T7 or SP6 cytoplasmic expression system is another possible embodiment. Eukaryotic cells can support cytoplasmic transcription from certain bacteriophage promoters if the appropriate bacteriophage polymerase is provided, either as part of the delivery complex or as an additional genetic expression vector.

TABLE 2

| ENHANCER |
|---|
| Immunoglobulin Heavy Chain |
| Immunoglobulin Light Chain |
| T-Cell Receptor |
| HLA DQ a and DQ β |
| β-Interferon |
| Interleukin-2 |
| Interleukin-2 Receptor |
| MHC Class II 5 |
| MHC Class II HLA-DRa |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| c-fos |
| c-HA-ras |
| Insulin |
| Neural Cell Adhesion Molecule (NCAM) |
| a1-Antitrypsin |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |

TABLE 2-continued

| ENHANCER |
|---|
| Polyoma |
| Retroviruses |
| Papilloma Virus |
| Hepatitis B Virus |
| Human Immunodeficiency Virus |
| Cytomegalovirus |
| Gibbon Ape Leukemia Virus |

Further, selection of a promoter that is regulated in response to specific physiologic signals can permit inducible expression of the SRF constructs, respectively. For example, with the polynucleotide under the control of the human PAI-1 promoter, expression is inducible by tumor necrosis factor. Table 3 illustrates several promoter/inducer combinations:

TABLE 3

| Element | Inducer |
|---|---|
| MT II Phorbol Ester (TFA) | Heavy metals |
| MMTV (mouse mammary tumor virus) | Glucocorticoids |
| β-Interferon | Poly(rI)XPoly(rc) |
| Adenovirus 5 E2 | Ela |
| c-jun | Phorbol Ester (TPA), H2O2 |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease |
| GRP78 Gene | A23187 |
| a-2-Macroglobulin | IL-6 |
| Vimentin | Serum |
| MHC Class I Gene H-2kB | Interferon |
| HSP70 Ela, SV40 Large T Antigen | |
| Proliferin | Phorbol Ester-TPA |
| Tumor Necrosis Factor | FMA |
| Thyroid Stimulating Hormone a Gene | Thyroid Hormone |

In certain embodiments of the invention, the delivery of an expression vector in a cell may be identified in vitro or in vivo by including a marker in the expression vector. The marker would result in an identifiable change to the transfected cell permitting easy identification of expression. Usually the inclusion of a drug selection marker aids in cloning and in the selection of transformants. Alternatively, enzymes such as herpes simplex virus thymidine kinase (tk) (eukaryotic) or chloramphenicol acetyltransferase (CAT) (prokaryotic) may be employed. Immunologic markers also can be employed. The selectable marker employed is not believed to be important, so long as it is capable of being expressed along with the polynucleotide encoding SRF. Further examples of selectable markers are well known to one of skill in the art.

One typically will include a polyadenylation signal to effect proper polyadenylation of the transcript. The nature of the polyadenylation signal is not believed to be crucial to the successful practice of the invention, and any such sequence may be employed. The inventor has employed the SV40 polyadenylation signal in that it was convenient and known to function well in the target cells employed. Also contemplated as an element of the expression construct is a terminator. These elements can serve to enhance message levels and to minimize read through from the construct into other sequences.

The expression construct may comprise a virus or engineered construct derived from a viral genome. The ability of certain viruses to enter cells via receptor-mediated endocytosis and, in some cases, integrate into the host cell chromosomes, have made them attractive candidates for gene transfer in to mammalian cells. However, because it has been demonstrated that direct uptake of naked DNA, as well as receptor-mediated uptake of DNA complexes, expression vectors need not be viral but, instead, may be any plasmid, cosmid or phage construct that is capable of supporting expression of encoded genes in mammalian cells, such as pUC or Bluescript™ plasmid series.

E. Rational Drug Design

The goal of rational drug design is to produce structural analogs of biologically active polypeptides or compounds with which they interact (agonists, antagonists, inhibitors, binding partners, etc.). By creating such analogs, it is possible to fashion drugs which are more active or stable than the natural molecules, which have different susceptibility to alteration, or which may affect the function of various other molecules. In one approach, one would generate a three-dimensional structure for SRF, for an uncleavable SRF, for a caspase inhibitor, or a fragment thereof. This could be accomplished by x-ray crystallography, computer modeling or by a combination of both approaches. An alternative approach, "alanine scan," involves the random replacement of residues throughout molecule with alanine, and the resulting affect on function determined.

It also is possible to isolate, for example, a SRF specific antibody, selected by a functional assay, and then solve its crystal structure. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs that have improved SRF activity or that act as stimulators, inhibitors, agonists, antagonists or SRF or molecules affected by SRF function. By use of cloned SRF sequences, sufficient amounts of SRF can be produced to perform crystallographic studies. In addition, knowledge of the polypeptide sequences permits computer employed predictions of structure-function relationships.

The present invention also contemplates the use of SRF and active fragments, and nucleic acids coding therefor, in the screening of compounds for activity in either stimulating SRF activity, overcoming the lack of SRF or blocking the effect of a mutant SRF molecule.

The present invention also encompasses the use of various animal models. By developing or isolating mutant cells lines that fail to express normal SRF, one can, in some embodiments, generate cardiac disease models in mice that will be highly predictive of same in humans and other mammals. Transgenic animals that lack a wild-type SRF may be utilized as models for cardiac disease development and treatment.

Treatment of animals with test compounds will involve the administration of the compound, in an appropriate form, to the animal. Administration will be by any route the could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply and intratumoral injection.

Determining the effectiveness of a compound in vivo may involve a variety of different criteria. Such criteria include, but are not limited to, survival, reduction of tumor burden or mass, arrest or slowing of tumor progression, elimination of tumors, inhibition or prevention of metastasis, increased activity level, improvement in immune effector function and improved food intake.

VII. Pharmaceutical Compositions and Routes of Administration

Compositions of the present invention may have an effective amount of a caspase inhibitor and/or uncleavable SRF for therapeutic administration for cardiac disease and, in some embodiments, in combination with an effective amount of a compound (second agent) that is an anti-cardiac disease agent. Such compositions will generally be dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, mouthwashes, inhalants and the like.

The expression vectors and delivery vehicles of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The vectors of the present invention are advantageously administered in the form of injectable compositions either as liquid solutions or suspensions; solid forms suitable for solution in, or suspension in, liquid prior to injection also may be prepared. These preparations also may be emulsified. A typical composition for such purposes comprises a 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters, such as theyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components in the pharmaceutical are adjusted according to well-known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual.

All the essential materials and reagents required for delivery of a caspase inhibitor and/or uncleavable SRF may be assembled together in a kit. When the components of the kit are provided in one or more liquid solutions, the liquid solution preferably is an aqueous solution, with a sterile aqueous solution being particularly preferred.

For in vivo use, an anti-cardiac disease agent may be formulated into a single or separate pharmaceutically acceptable syringeable composition. In this case, the container means may itself be an inhalant, syringe, pipette, eye dropper, or other such like apparatus, from which the formulation may be applied to an infected area of the body, such as the lungs, injected into an animal, or even applied to and mixed with the other components of the kit.

The components of the kit may also be provided in dried or lyophilized forms. When reagents or components are provided as a dried form, reconstitution generally is by the addition of a suitable solvent. It is envisioned that the solvent also may be provided in another container means. The kits of the invention may also include an instruction sheet defining administration of the gene therapy and/or the anti-cardiac disease drug.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye-dropper or any such medically approved delivery vehicle.

The active compounds of the present invention will often be formulated for parenteral administration, e.g., formulated for injection via the intravenous, intramuscular, subcutaneous, or even intraperitoneal routes. The preparation of an aqueous composition that contains a second agent(s) as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in cremes and lotions.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Targeting of cardiovascular tissues may be accomplished in any one of a variety of ways. Plasmid vectors and retroviral vectors, adenovirus vectors, and other viral vectors all present means by which to target cardiovascular tissue. The inventors anticipate particular success for the use of liposomes to target SRF, caspase inhibitor and/or uncleavable SRF to cells, to cardiac tissue. For example, DNA encoding SRF or uncleavable may be complexed with liposomes in the manner described above, and this DNA/liposome complex is injected into patients with cardiac disease, intravenous injection can be used to direct the gene to all cell. Directly injecting the liposome complex into the proximity of the diseased tissue can also provide for targeting of the complex with some forms of cardiac disease. Of course, the potential for liposomes that are selectively taken up by a population of cells exists, and such liposomes will also be useful for targeting the gene.

Those of skill in the art will recognize that the best treatment regimens for using SRF, an uncleavable SRF, and/or a caspase inhibitor to prevent and/or to treat diseased cardiac tissue can be straightforwardly determined. This is not a question of experimentation, but rather one of optimization, which is routinely conducted in the medical arts. In one exemplary embodiment, in vivo studies in nude mice provide a starting point from which to begin to optimize the dosage and delivery regimes. The frequency of injection will initially be once a wk, as was done some mice studies. However, this frequency might be optimally adjusted from one day to every two weeks to monthly, depending upon the results obtained from the initial clinical trials and the needs of a particular patient. Human dosage amounts can initially be determined by extrapolating from the amount of SRF used in mice. In certain embodiments it is envisioned that the dosage may vary from between about 1 mg SRF DNA/Kg body weight to about 5000 mg SRF DNA/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, 5000 mg/Kg body weight. In other embodiments, it is envisaged that higher does may be used, such doses may be in the range of about 5 mg SRF DNA/Kg body to about 20 mg SRF DNA/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

VIII. In vivo Delivery and Treatment Protocols

Where the gene itself is employed to introduce the gene products, a convenient method of introduction will be through the use of a recombinant vector or vectors that incorporates the desired gene(s), together with its associated control sequences. The preparation of recombinant vectors is well known to those of skill in the art and described in many references, such as, for example, Sambrook et al. (1989), specifically incorporated herein by reference.

In vectors, it is understood that the DNA coding sequences to be expressed, in this case those encoding the SRF gene products, are positioned adjacent to and under the control of a promoter. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter. One may also desire to incorporate into the transcriptional unit of the vector an appropriate polyadenylation site (e.g., 5'-AATAAA-3'), if one was not contained within the original inserted DNA. Typically, these poly A addition sites are placed about 30 to 2000 nucleotides "downstream" of the coding sequence at a position prior to transcription termination.

While use of the control sequences of the SRF will be preferred, there is no reason why other control sequences could not be employed, so long as they are compatible with the genotype of the cell being treated. Thus, one may mention other useful promoters by way of example, including, e.g., an SV40 early promoter, a long terminal repeat promoter from retrovirus, an actin promoter, a heat shock promoter, a metallothionein promoter, and the like.

For introduction of the SRF gene, it is proposed that one will desire to preferably employ a vector construct that will deliver the desired gene to the affected cells. This will, of course, generally require that the construct be delivered to the targeted tumor cells, for example, breast, genital, or lung tumor cells. It is proposed that this may be achieved most preferably by introduction of the desired gene through the use of a viral or non-viral vector or vectors to carry the SRF sequences to efficiently transfect a cell. This infection may be achieved preferably by liposomal delivery but may also be via adenoviral, a retroviral, a vaccinia virus, herpesvirus or adeno-associated virus vector, or a combination thereof. These vectors have been successfully used to deliver desired sequences to cells and tend to have a high infection efficiency.

Commonly used viral promoters for expression vectors are derived from polyoma, cytomegalovirus, Adenovirus 2, and Simian Virus 40 (SV40). The early and late promoters of SV40 virus are particularly useful because both are obtained easily from the virus as a fragment that also contains the SV40 viral origin of replication. Smaller or larger SV40 fragments may also be used, provided there is included the approximately 250 bp sequence extending from the HindIII site toward the Bgl I site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

A. Liposomal Transfection

The expression construct may be entrapped in a liposome. Liposomes are structures created by mixing phospholipids with water, or hydration of phospholipid. The resultant bilayer structures tend to fold back upon themselves. Liposomes are frequently multilamellar, composed of concentric bilayer membranes separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

The present invention also provides particularly useful methods for introducing SRF gene products into cells. One method of in vivo gene transfer that can lead to expression of genes transfected into cells involves the use of liposomes. Liposomes can be used for both in vitro and in vivo transfection. Liposome-mediated gene transfer seems to have great potential for certain in vivo applications in animals (Nicolau et al., 1987). Studies have shown that intravenously injected liposomes are taken up essentially in the liver and the spleen, by the macrophages of the reticuloendothelial system. The specific cellular sites of uptake of injected liposomes appears to be mainly spleen macrophages and liver Kupffer cells. Intravenous injection of liposomes/DNA complexes can lead to the uptake of DNA by these cellular sites, and result in the expression of a gene product encoded in the DNA (Nicolau, 1982).

The inventors contemplate that SRF gene products can be introduced into cells using liposome-mediated gene transfer. It is proposed that such constructs can be coupled with liposomes and directly introduced via a catheter, as described by Nabel et al. (1990). By employing these methods, SRF gene products can be expressed efficiently at a specific site in vivo, not just the liver and spleen cells which are accessible via intravenous injection. Therefore, this invention also encompasses compositions of DNA constructs encoding an SRF gene product formulated as a DNA/liposome complex and methods of using such constructs.

Liposomal transfection can be via liposomes composed of, for example, phosphatidylcholine (PC), phosphatidylserine (PS), cholesterol (Chol), N-[1-(2,3-dioleyloxy)propyl]-N,N-trimethylammonium chloride (DOTMA), dioleoylphosphatidyl-ethanolamine (DOPE), and/or 3b[N-(N'N'-dimethylaminoethane)-carbarmoyl cholesterol (DC-Chol), as well as other lipids known to those of skill in the art. Those of skill in the art will recognize that there are a variety of liposomal transfection techniques that will be useful in the present invention. Among these techniques are those described in Nicolau et al., 1987, Nabel et al., 1990, and Gao et al., 1991. In one embodiment of the present invention, liposomes comprising DC-Chol and DOPE that have been prepared following the teaching of Gao et al., 1991, are used. The inventors also anticipate utility for liposomes comprised of DOTMA, such as those that are available commercially under the trademark Lipofectin™, from Vical, Inc., in San Diego, Calif.

Liposomes may be introduced into contact with cells to be transfected by a variety of methods. In cell culture, the liposome-DNA complex can simply be dispersed in the cell culture solution. For application in vivo, liposome-DNA complex are typically injected. Intravenous injection allows liposome-mediated transfer of DNA complex, for example, the liver and the spleen. In order to allow transfection of DNA into cells which are not accessible through intravenous injection, it is possible to directly inject the liposome-DNA complexes into a specific location in an animal's body. For example, Nabel et al. teach injection via a catheter into the arterial wall. In another example, the inventors have used intraperitoneal injection to allow for gene transfer into mice.

The present invention also contemplates compositions comprising a liposomal complex. This liposomal complex will comprise a lipid component and a DNA segment encoding a SRF polynucleotide.

The lipid employed to make the liposomal complex can be any of the above-discussed lipids. In particular, DOTMA, DOPE, and/or DC-Chol may form all or part of the liposomal complex. The inventors have had particular success with complexes comprising DC-Chol. In a preferred embodiment, the lipid will comprise DC-Chol and DOPE. While any ratio of DC-Chol to DOPE is expected to have utility, it is expected that those comprising a ratio of DC-Chol:DOPE between 1:20 and 20:1 will be particularly advantageous. The inventors have found that liposomes prepared from a ratio of DC-Chol:DOPE of about 1:10 to about 1:5 have been useful.

It is proposed that it will ultimately be preferable to employ the smallest region needed to suppress the SRF polynucleotide so that one is not introducing unnecessary DNA into cells which receive a SRF polynucleotide construct. Techniques well known to those of skill in the art, such as the use of restriction enzymes, will allow for the generation of small regions of SRF. The ability of these regions to promote smooth muscle cell differentiation can easily be determined by the assays reported in the Examples.

In certain embodiments of the invention, the liposome may be complexed with a hemagglutinatin virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of polynucleotide in vitro and in vivo, then they are applicable for the present invention. Where a bacterial promoter is employed in the DNA construct, it also will be desirable to include within the liposome an appropriate bacterial polymerase.

B. Adenovirus

Another method for in vivo delivery involves the use of an adenovirus vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

Adenovirus is a particularly suitable gene transfer vector because of its midsized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, located at 16.8 mm is particularly efficient during the late phase of infection, and all the mRNA's issued from this promoter possess a 5'-tripartite leader (TL) sequence which makes them preferred mRNA's for translation.

In some cases, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure. Use of the YAC system is an alternative approach for the production of recombinant adenovirus.

A particular method of introducing the SRF to an animal is to introduce at least one replication-deficient adenovirus comprising the SRF polynucleotide. The replication-deficient construct made by E1B and E3 deletion also avoids the viral reproduction inside the cell and transfer to other cells and infection of other people, which means the viral infection activity is shut down after it infects the target cell. The SRF gene is still expressed inside the cells. Also, unlike retrovirus, which can only infect proliferating cells, adenovirus is able to transfer the SRF gene into both proliferating and non-proliferating cells. Further, the extrachromosomal location of adenovirus in the infected cells decreases the chance of cellular oncogene activation within the treated animal.

Introduction of the adenovirus containing the SRF gene product gene into a suitable host is typically done by injecting the virus contained in a buffer.

The nature of the adenovirus vector is not believed to be crucial to the successful practice of the invention. Of course, as discussed above, it is advantageous if the adenovirus vector is replication defective, or at least conditionally defective. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

Adenovirus is easy to grow and manipulate and exhibits broad host range in vitro and in vivo. This group of viruses can be obtained in high titers, e.g., 109-1011 plaque-forming units per ml, and they are highly infective. The life cycle of adenovirus does not require integration in to the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus have been used in eukaryotic gene expression (Levrero et al., 1991; Gomez-Foix et al., 1992) and vaccine development (Grunhaus and Horwitz, 1992; Graham and Prevec, 1992). Animal studies have suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotatic inoculation into the brain (Le Gal La Salle et al., 1993).

C. Retroviruses

The retroviruses are a group of single-stranded RNA viruses characterized by an ability to convert their RNA to double-stranded DNA to infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene, termed y components is constructed (Mann et al., 1983). When a recombinant plasmid containing a human cDNA, together with the retroviral LTR and y sequences is introduced into this cell line (by calcium phosphate precipitation for example), the y sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. One limitation to the use of retrovirus vectors in vivo is the limited ability to produce retroviral vector titers greater than 106 infections U/mL. Titers 10- to 1,000-fold higher are necessary for many in vivo applications.

Several properties of the retrovirus have limited its use in lung cancer treatment (Stratford-Perricaudet and Perricaudet, 1991; (i) Infection by retrovirus depends on host cell division. In human cancer, very few mitotic cells can be found in tumor lesions. (ii) The integration of retrovirus into the host genome may cause adverse effects on target cells, because malignant cells are high in genetic instability. (iii) Retrovirus infection is often limited by a certain host range. (iv) Retrovirus has been associated with many malignancies in both mammals and vertebrates. (v) The titer of retrovirus, in general, is 100- to 1,000-fold lower than that of adenovirus.

In one embodiment of the present invention, the SRF polynucleotide(s) are comprised on at least 1 retroviral vector.

D. Other Viral Vectors as Expression Constructs

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpes viruses may be employed. They offer several attractive features for various mammalian cells (Friedmann, 1989; Ridgeway, 1988; Baichwal and Sugden, 1986; Coupar et al., 1988; Howrich et al., 1990).

With the recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Cultures media containing high titers of the recombinant virus were used to infect primary duckling hepatocytes. Stable CAT gene expression was detected for at least 24 days after transfection (Chang et al., 1991).

E. Other Non-viral Vectors

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. As described above, delivery may be via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the polynucleotide encoding the gene of interest may be positioned and expressed at different sites. In certain embodiments, the polynucleotide encoding the gene may be stably maintained in the cell as a separate, episomal segment of DNA. Such polynucleotide segments or "episomes" encode sequences sufficient to permit maintenance and replication independent of or in synchronization with the host cell cycle. How the expression construct is delivered to a cell and where in the cell the polynucleotide remains is dependent on the type of expression construct employed.

In one embodiment of the invention, the expression construct or constructs may simply consist of naked recombinant DNA or plasmids. Transfer of the construct may be performed by any of the methods mentioned above which physically or chemically permeabilize the cell membrane. This is particularly applicable for transfer to permeabilize the cell membrane. This is particularly applicable for transfer in vitro but it may be applied to in vivo use as well. Dubensky et al. (1984) successfully injected polyomavirus DNA in the form of CaPO4 precipitates into liver and spleen of adult and newborn mice demonstrating active viral replication and acute infection. Benvenisty and Reshef (1986) also demonstrated that direct intraperitoneal injection of CaPO4 precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

Other expression constructs which can be employed to deliver a polynucleotide encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific.

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). A synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a polynucleotide encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a polynucleotide encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a polynucleotide into the cells, in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods.

F. Protein Therapy

Another therapy approach is the provision, to a subject, of SRF, CRP, and/or GATA polypeptide, active fragments, synthetic peptides, mimetics or other analogs thereof. The protein may be produced by recombinant expression means or, if small enough, generated by an automated peptide synthesizer. Formulations would be selected based on the route of administration and purpose including, but not limited to, liposomal formulations and classic pharmaceutical preparations.

G. Lipid Compositions

In certain embodiments, the present invention concerns a novel composition comprising one or more lipids associated with at least one SRF polynucleotide or SRF polypeptide, protein, or peptide. A lipid is a substance that is characteristically insoluble in water and extractable with an organic solvent. Lipids include, for example, the substances comprising the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes. Of course, compounds other than those specifically described herein that are understood by one of skill in the art as lipids are also encompassed by the compositions and methods of the present invention.

A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof.

1. Lipid Types

A neutral fat may comprise a glycerol and a fatty acid. A typical glycerol is a three carbon alcohol. A fatty acid generally is a molecule comprising a carbon chain with an acidic moeity (e.g., carboxylic acid) at an end of the chain. The carbon chain may of a fatty acid may be of any length, however, it is preferred that the length of the carbon chain be of from about 2, about 3, about 4, about 5, about 6, about 7, about 8, about 9, about 10, about 11 about 12, about 13, about 14, about 15, about 16, about 17, about 18, about 19, about 20, about 21, about 22, about 23, about 24, about 25, about 26, about 27, about 28, about 29, to about 30 or more carbon atoms, and any range derivable therein. However, a preferred range is from about 14 to about 24 carbon atoms in the chain portion of the fatty acid, with about 16 to about 18 carbon atoms being particularly preferred in certain embodiments. In certain embodiments the fatty acid carbon chain may comprise an odd number of carbon atoms, however, an even number of carbon atoms in the chain may be preferred in certain embodiments. A fatty acid comprising only single bonds in its carbon chain is called saturated, while a fatty acid comprising at least one double bond in its chain is called unsaturated.

Specific fatty acids include, but are not limited to, linoleic acid, oleic acid, palmitic acid, linolenic acid, stearic acid, lauric acid, myristic acid, arachidic acid, palmitoleic acid, arachidonic acid, ricinoleic acid, tuberculosteric acid, lactobacillic acid. An acidic group of one or more fatty acids is covalently bonded to one or more hydroxyl groups of a glycerol. Thus, a monoglyceride comprises a glycerol and one fatty acid, a diglyceride comprises a glycerol and two fatty acids, and a triglyceride comprises a glycerol and three fatty acids.

A phospholipid generally comprises either glycerol or an sphingosine moiety, an ionic phosphate group to produce an amphipathic compound, and one or more fatty acids. Types of phospholipids include, for example, phophoglycerides, wherein a phosphate group is linked to the first carbon of glycerol of a diglyceride, and sphingophospholipids (e.g., sphingomyelin), wherein a phosphate group is esterified to a sphingosine amino alcohol. Another example of a sphingophospholipid is a sulfatide, which comprises an ionic sulfate group that makes the molecule amphipathic. A phopholipid may, of course, comprise further chemical groups, such as for example, an alcohol attached to the phosphate group. Examples of such alcohol groups include serine, ethanolamine, choline, glycerol and inositol. Thus, specific phosphoglycerides include a phosphatidyl serine, a phosphatidyl ethanolamine, a phosphatidyl choline, a phosphatidyl glycerol or a phosphotidyl inositol. Other phospholipids include a phosphatidic acid or a diacetyl phosphate. In one aspect, a phosphatidylcholine comprises a dioleoylphosphatidylcholine (a.k.a. cardiolipin), an egg phosphatidylcholine, a dipalmitoyl phosphalidycholine, a monomyristoyl phosphatidylcholine, a monopalmitoyl phosphatidylcholine, a monostearoyl phosphatidylcholine, a monooleoyl phosphatidylcholine, a dibutroyl phosphatidylcholine, a divaleroyl phosphatidylcholine, a dicaproyl phosphatidylcholine, a diheptanoyl phosphatidylcholine, a dicapryloyl phosphatidylcholine or a distearoyl phosphatidylcholine.

A glycolipid is related to a sphinogophospholipid, but comprises a carbohydrate group rather than a phosphate group attached to a primary hydroxyl group of the sphingosine. A type of glycolipid called a cerebroside comprises one sugar group (e.g., a glucose or galactose) attached to the primary hydroxyl group. Another example of a glycolipid is a ganglioside (e.g., a monosialoganglioside, a GM1), which comprises about 2, about 3, about 4, about 5, about 6, to about 7 or so sugar groups, that may be in a branched chain, attached to the primary hydroxyl group. In other embodiments, the glycolipid is a ceramide (e.g., lactosylceramide).

A steroid is a four-membered ring system derivative of a phenanthrene. Steroids often possess regulatory functions in cells, tissues and organisms, and include, for example, hormones and related compounds in the progestagen (e.g., progesterone), glucocoricoid (e.g., cortisol), mineralocorticoid (e.g., aldosterone), androgen (e.g., testosterone) and estrogen (e.g., estrone) families. Cholesterol is another example of a steroid, and generally serves structural rather than regulatory functions. Vitamin D is another example of a sterol, and is involved in calcium absorption from the intestine.

A terpene is a lipid comprising one or more five carbon isoprene groups. Terpenes have various biological functions, and include, for example, vitamin A, coenyzme Q and carotenoids (e.g., lycopene and β-carotene).

2. Charged and Neutral Lipid Compositions

In certain embodiments, a lipid component of a composition is uncharged or primarily uncharged. In one embodiment, a lipid component of a composition comprises one or more neutral lipids. In another aspect, a lipid component of a composition may be substantially free of anionic and cationic lipids, such as certain phospholipids (e.g., phosphatidyl choline) and cholesterol. In certain aspects, a lipid component of an uncharged or primarily uncharged lipid composition comprises about 95%, about 96%, about 97%, about 98%, about 99% or 100% lipids without a charge, substantially uncharged lipid(s), and/or a lipid mixture with equal numbers of positive and negative charges.

In other aspects, a lipid composition may be charged. For example, charged phospholipids may be used for preparing a lipid composition according to the present invention and can carry a net positive charge or a net negative charge. In a non-limiting example, diacetyl phosphate can be employed to confer a negative charge on the lipid composition, and stearylamine can be used to confer a positive charge on the lipid composition.

3. Making Lipids

Lipids can be obtained from natural sources, commercial sources or chemically synthesized, as would be known to one of ordinary skill in the art. For example, phospholipids can be from natural sources, such as egg or soybean phosphatidylcholine, brain phosphatidic acid, brain or plant phosphatidylinositol, heart cardiolipin and plant or bacterial phosphatidylethanolamine. In another example, lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). In certain embodiments, stock solutions of lipids in chloroform or chloroform/methanol can be stored at about −20° C. Preferably, chloroform is used as the only solvent since it is more readily evaporated than methanol.

4. Lipid Composition Structures

In a preferred embodiment of the invention, the SRF, CRP, and/or GATA composition may be associated with a lipid. A SRF, CRP, and/or GATA composition associated with a lipid may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure. A lipid or lipid/SRF, CRP, and/or GATA composition associated composition of the present invention is not limited to any particular structure. For example, they may also simply be interspersed in a solution, possibly forming aggregates which are not uniform in either size or shape. In another example, they may be present in a bilayer structure, as micelles, or with a "collapsed" structure. In another non-limiting example, a lipofectamine(Gibco BRL)-SRF, CRP, and/or GATA composition or Superfect (Qiagen)-SRF, CRP, and/or GATA composition complex is also contemplated.

In certain embodiments, a lipid composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, or any range derivable therein, of a particular lipid, lipid type or non-lipid component such as a drug, protein, sugar, nucleic acids or other material disclosed herein or as would be known to one of skill in the art. In a non-limiting example, a lipid composition may comprise about 10% to about 20% neutral lipids, and about 33% to about 34% of a cerebroside, and about 1% cholesterol. In another non-limiting example, a liposome may comprise about 4% to about 12% terpenes, wherein about 1% of the micelle is specifically lycopene, leaving about 3% to about 11% of the liposome as comprising other terpenes; and about 10% to about 35% phosphatidyl choline, and about 1% of a drug. Thus, it is contemplated that lipid compositions of the present invention may comprise any of the lipids, lipid types or other components in any combination or percentage range.

5. Emulsions

A lipid may be comprised in an emulsion. A lipid emulsion is a substantially permanent heterogenous liquid mixture of two or more liquids that do not normally dissolve in each other, by mechanical agitation or by small amounts of additional substances known as emulsifiers. Methods for preparing lipid emulsions and adding additional components are well known in the art (e.g., Modern Pharmaceutics, 1990, incorporated herein by reference).

For example, one or more lipids are added to ethanol or chloroform or any other suitable organic solvent and agitated by hand or mechanical techniques. The solvent is then evaporated from the mixture leaving a dried glaze of lipid. The lipids are resuspended in aqueous media, such as phosphate buffered saline, resulting in an emulsion. To achieve a more homogeneous size distribution of the emulsified lipids, the mixture may be sonicated using conventional sonication techniques, further emulsified using microfluidization (using, for example, a Microfluidizer, Newton, Mass.), and/or extruded under high pressure (such as, for example, 600 psi) using an Extruder Device (Lipex Biomembranes, Vancouver, Canada).

6. Micelles

A lipid may be comprised in a micelle. A micelle is a cluster or aggregate of lipid compounds, generally in the form of a lipid monolayer, and may be prepared using any micelle producing protocol known to those of skill in the art (e.g., Canfield et al., 1990; El-Gorab et al., 1973; Colloidal Surfactant, 1963; and Catalysis in Micellar and Macromolecular Systems, 1975, each incorporated herein by reference). For example, one or more lipids are typically made into a suspension in an organic solvent, the solvent is evaporated, the lipid is resuspended in an aqueous medium, sonicated and then centrifuged.

7. Liposomes

In particular embodiments, a lipid comprises a liposome. A "liposome" is a generic term encompassing a variety of single and multilamellar lipid vehicles formed by the generation of enclosed lipid bilayers or aggregates. Liposomes may be characterized as having vesicular structures with a bilayer membrane, generally comprising a phospholipid, and an inner medium that generally comprises an aqueous composition.

A multilamellar liposome has multiple lipid layers separated by aqueous medium. They form spontaneously when lipids comprising phospholipids are suspended in an excess of aqueous solution. The lipid components undergo self-rearrangement before the formation of closed structures and entrap water and dissolved solutes between the lipid bilayers (Ghosh and Bachhawat, 1991). Lipophilic molecules or molecules with lipophilic regions may also dissolve in or associate with the lipid bilayer.

In certain less preferred embodiments, phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition or a liposome, because of the instability and leakiness of the resulting liposomes.

In particular embodiments, a SRF composition may be, for example, encapsulated in the aqueous interior of a liposome, interspersed within the lipid bilayer of a liposome, attached to a liposome via a linking molecule that is associated with both the liposome and the SRF composition, entrapped in a liposome, complexed with a liposome, etc.

8. Making Liposomes

A liposome used according to the present invention can be made by different methods, as would be known to one of ordinary skill in the art. Phospholipids can form a variety of structures other than liposomes when dispersed in water, depending on the molar ratio of lipid to water. At low ratios the liposome is the preferred structure.

For example, a phospholipid (Avanti Polar Lipids, Alabaster, Ala.), such as for example the neutral phospholipid dioleoylphosphatidylcholine (DOPC), is dissolved in tert-butanol. The lipid(s) is then mixed with the SRF composition, and/or other component(s). Tween 20 is added to the lipid mixture such that Tween 20 is about 5% of the composition's weight. Excess tert-butanol is added to this mixture such that the volume of tert-butanol is at least 95%. The mixture is vortexed, frozen in a dry ice/acetone bath and lyophilized overnight. The lyophilized preparation is stored at −20° C. and can be used up to three months. When required the lyophilized liposomes are reconstituted in 0.9% saline. The average diameter of the particles obtained using Tween 20 for encapsulating the SRF composition is about 0.7 to about 1.0 mm in diameter.

Alternatively, a liposome can be prepared by mixing lipids in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25-50 mM phospholipid in sterile, pyrogen-free water by shaking until all the lipid film is resuspended. The aqueous liposomes can be then separated into aliquots, each placed in a vial, lyophilized and sealed under vacuum.

In other alternative methods, liposomes can be prepared in accordance with other known laboratory procedures (e.g., see Bangham et al., 1965; Gregoriadis, 1979; Deamer and Uster 1983, Szoka and Papahadjopoulos, 1978, each incorporated herein by reference in relevant part). These methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated additional materials, such as agents including but not limited to hormones, drugs, nucleic acid constructs and the like, are removed by centrifugation at 29,000×g and the liposomal pellets washed. The washed liposomes are resuspended at an appropriate total phospholipid concentration, e.g., about 50-200 mM. The amount of additional material or active agent encapsulated can be determined in accordance with standard methods. After determination of the amount of additional material or active agent encapsulated in the liposome preparation, the liposomes may be diluted to appropriate concentrations and stored at 4° C. until use. A pharmaceutical composition comprising the liposomes will usually include a sterile, pharmaceutically acceptable carrier or diluent, such as water or saline solution.

The size of a liposome varies depending on the method of synthesis. Liposomes in the present invention can be a variety of sizes. In certain embodiments, the liposomes are small, e.g., less than about 100 nm, about 90 nm, about 80 nm, about 70 nm, about 60 nm, or less than about 50 nm in external diameter. In preparing such liposomes, any protocol described herein, or as would be known to one of ordinary skill in the art may be used. Additional non-limiting examples of preparing liposomes are described in U.S. Pat. Nos. 4,728,578, 4,728,575, 4,737,323, 4,533,254, 4,162,282, 4,310,505, and 4,921,706; International Applications PCT/US85/01161 and PCT/US89/05040; U.K. Patent Application GB 2193095 A; Mayer et al., 1986; Hope et al., 1985; Mayhew et al., 1987; Mayhew et al., 1984; Cheng et al., 1987; and Liposome Technology, 1984, each incorporated herein by reference).

A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

The production of lipid formulations often is accomplished by sonication or serial extrusion of liposomal mixtures after (I) reverse phase evaporation (II) dehydration-rehydration (III) detergent dialysis and (IV) thin film hydration. In one aspect, a contemplated method for preparing liposomes in certain embodiments is heating sonicating, and sequential extrusion of the lipids through filters or membranes of decreasing pore size, thereby resulting in the formation of small, stable liposome structures. This preparation produces liposomal/SRF, CRP, and/or GATA composition or liposomes only of appropriate and uniform size, which are structurally stable and produce maximal activity. Such techniques are well-known to those of skill in the art (see, for example Martin, 1990).

Once manufactured, lipid structures can be used to encapsulate compounds that are toxic (e.g., chemotherapeutics) or labile (e.g., nucleic acids) when in circulation. The physical characteristics of liposomes depend on pH, ionic strength and/or the presence of divalent cations. Liposomes can show low permeability to ionic and/or polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and/or results in an increase in permeability to ions, sugars and/or drugs. Liposomal encapsulation has resulted in a lower toxicity and a longer serum half-life for such compounds (Gabizon et al., 1990).

Liposomes interact with cells to deliver agents via four different mechanisms: Endocytosis by phagocytic cells of the reticuloendothelial system such as macrophages and/or neutrophils; adsorption to the cell surface, either by nonspecific weak hydrophobic and/or electrostatic forces, and/or by specific interactions with cell-surface components; fusion with the plasma cell membrane by insertion of the lipid bilayer of the liposome into the plasma membrane, with simultaneous release of liposomal contents into the cytoplasm; and/or by transfer of liposomal lipids to cellular and/or subcellular membranes, and/or vice versa, without any association of the liposome contents. Varying the liposome formulation can alter which mechanism is operative, although more than one may operate at the same time.

Numerous disease treatments are using lipid based gene transfer strategies to enhance conventional or establish novel therapies, in particular therapies for treating hyperproliferative diseases. Advances in liposome formulations have improved the efficiency of gene transfer in vivo (Templeton et al., 1997) and it is contemplated that liposomes are prepared by these methods. Alternate methods of preparing lipid-based formulations for nucleic acid delivery are described (WO 99/18933).

In another liposome formulation, an amphipathic vehicle called a solvent dilution microcarrier (SDMC) enables integration of particular molecules into the bi-layer of the lipid vehicle (U.S. Pat. No. 5,879,703). The SDMCs can be used to deliver lipopolysaccharides, polypeptides, nucleic acids and the like. Of course, any other methods of liposome preparation can be used by the skilled artisan to obtain a desired liposome formulation in the present invention.

9. Liposome Targeting

Association of the SRF composition with a liposome may improve biodistribution and other properties of the SRF composition. For example, liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980). Successful liposome-mediated gene transfer in rats after intravenous injection has also been accomplished (Nicolau et al., 1987).

It is contemplated that a liposome/SRF composition may comprise additional materials for delivery to a tissue. For example, in certain embodiments of the invention, the lipid or liposome may be associated with a hemagglutinating virus (HVJ). This has been shown to facilitate fusion with the cell membrane and promote cell entry of liposome-encapsulated DNA (Kaneda et al., 1989). In another example, the lipid or liposome may be complexed or employed in conjunction with nuclear non-histone chromosomal proteins (HMG-1) (Kato et al., 1991). In yet further embodiments, the lipid may be complexed or employed in conjunction with both HVJ and HMG-1.

Targeted delivery is achieved by the addition of ligands without compromising the ability of these liposomes deliver large amounts of a SRF composition. It is contemplated that this will enable delivery to specific cells, tissues and organs. The targeting specificity of the ligand-based delivery systems are based on the distribution of the ligand receptors on different cell types. The targeting ligand may either be non-covalently or covalently associated with the lipid complex, and can be conjugated to the liposomes by a variety of methods.

10. Cross-linkers

Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

Exemplary methods for cross-linking ligands to liposomes are described in U.S. Pat. Nos. 5,603,872 and 5,401,511, each specifically incorporated herein by reference in its entirety). Various ligands can be covalently bound to liposomal surfaces through the cross-linking of amine residues. Liposomes, in particular, multilamellar vesicles (MLV) or unilamellar vesicles such as microemulsified liposomes (MEL) and large unilamellar liposomes (LUVET), each containing phosphatidylethanolamine (PE), have been prepared by established procedures. The inclusion of PE in the liposome provides an active functional residue, a primary amine, on the liposomal surface for cross-linking purposes. Ligands such as epidermal growth factor (EGF) have been successfully linked with PE-liposomes. Ligands are bound covalently to discrete sites on the liposome surfaces. The number and surface density of these sites will be dictated by the liposome formulation and the liposome type. The liposomal surfaces may also have sites for non-covalent association. To form covalent conjugates of ligands and liposomes, cross-linking reagents have been studied for effectiveness and biocompatibility. Cross-linking reagents include glutaraldehyde (GAD), bifunctional oxirane (OXR), ethylene glycol diglycidyl ether (EGDE), and a water soluble carbodiimide, preferably 1-ethyl-3-(3-dimethylaminopropyl) carbodiimide (EDC). Through the complex chemistry of cross-linking, linkage of the amine residues of the recognizing substance and liposomes is established.

In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides and sugars.

In instances where a particular polypeptide does not contain a residue amenable for a given cross-linking reagent in its native sequence, conservative genetic or synthetic amino acid changes in the primary sequence can be utilized.

11. Targeting Ligands

The targeting ligand can be either anchored in the hydrophobic portion of the complex or attached to reactive terminal groups of the hydrophilic portion of the complex. The targeting ligand can be attached to the liposome via a linkage to a reactive group, e.g., on the distal end of the hydrophilic polymer. Preferred reactive groups include amino groups, carboxylic groups, hydrazide groups, and thiol groups. The coupling of the targeting ligand to the hydrophilic polymer can be performed by standard methods of organic chemistry that are known to those skilled in the art. In certain embodiments, the total concentration of the targeting ligand can be from about 0.01 to about 10% mol.

Targeting ligands are any ligand specific for a characteristic component of the targeted region. Preferred targeting ligands include proteins such as polyclonal or monoclonal antibodies, antibody fragments, or chimeric antibodies, enzymes, or hormones, or sugars such as mono-, oligo- and poly-saccharides (see, Heath et al., Chem. Phys. Lipids 40:347 (1986)) For example, disialoganglioside GD2 is a tumor antigen that has been identified neuroectodermal origin tumors, such as neuroblastoma, melanoma, small-cell lung carcenoma, glioma and certain sarcomas (Mujoo et al., 1986, . Schulz et al., 1984). Liposomes containing anti-disialoganglioside GD2 monoclonal antibodies have been used to aid the targeting of the liposomes to cells expressing the tumor antigen (Montaldo et al., 1999; Pagan et al., 1999). In another non-limiting example, breast and gynecological cancer antigen specific antibodies are described in U.S. Pat. No. 5,939,277, incorporated herein by reference. In a further non-limiting example, prostate cancer specific antibodies are disclosed in U.S. Pat. No. 6,107,090, incorporated herein by reference. Thus, it is contemplated that the antibodies described herein or as would be known to one of ordinary skill in the art may be used to target specific tissues and cell types in combination with the compositions and methods of the present invention. In certain embodiments of the invention, contemplated targeting ligands interact with integrins, proteoglycans, glycoproteins, receptors or transporters. Suitable ligands include any that are specific for cells of the target organ, or for structures of the target organ exposed to the circulation as a result of local pathology, such as tumors.

In certain embodiments of the present invention, in order to enhance the transduction of cells, to increase transduction of target cells, or to limit transduction of undesired cells, antibody or cyclic peptide targeting moieties (ligands) are associated with the lipid complex. Such methods are known in the art. For example, liposomes have been described further that specifically target cells of the mammalian central nervous system (U.S. Pat. No. 5,786,214, incorporated herein by reference). The liposomes are composed essentially of N-glutarylphosphatidylethanolamine, cholesterol and oleic acid, wherein a monoclonal antibody specific for neuroglia is conjugated to the liposomes. It is contemplated that a monoclonal antibody or antibody fragment may be used to target delivery to specific cells, tissues, or organs in the animal, such as for example, brain, heart, lung, liver, etc.

Still further, a SRF composition may be delivered to a target cell via receptor-mediated delivery and/or targeting vehicles comprising a lipid or liposome. These take advantage of the selective uptake of macromolecules by receptor-mediated endocytosis that will be occurring in a target cell. In view of the cell type-specific distribution of various receptors, this delivery method adds another degree of specificity to the present invention.

Thus, in certain aspects of the present invention, a ligand will be chosen to correspond to a receptor specifically expressed on the target cell population. A cell-specific SRF composition delivery and/or targeting vehicle may comprise a specific binding ligand in combination with a liposome. The SRF composition to be delivered is housed within a liposome and the specific binding ligand is functionally incorporated into a liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In certain embodiments, a receptor-mediated delivery and/or targeting vehicles comprise a cell receptor-specific ligand and a SRF composition-binding agent. Others comprise a cell receptor-specific ligand to which SRF composition to be delivered has been operatively attached. For example, several ligands have been used for receptor-mediated gene transfer (Wu and Wu, 1987; Wagner et al., 1990; Perales et al., 1994; Myers, EPO 0273085), which establishes the operability of the technique. In another example, specific delivery in the context of another mammalian cell type has been described (Wu and Wu, 1993; incorporated herein by reference).

In still further embodiments the: specific binding ligand may comprise one or more lipids or glycoproteins that direct cell-specific binding. For example, lactosy-ceramide, a galactose-terminal asialganglioside, have been incorporated into liposomes and observed an increase in the uptake of the insulin gene by hepatocytes (Nicolau et al., 1987). The asialoglycoprotein, asialofetuin, which contains terminal galactosyl residues, also has been demonstrated to target liposomes to the liver (Spanjer and Scherphof, 1983; Hara et al., 1996). The sugars mannosyl, fucosyl or N-acetyl glucosamine, when coupled to the backbone of a polypeptide, bind the high affinity manose receptor (U.S. Pat. No. 5,432,260, specifically incorporated herein by reference in its entirety). It is contemplated that the cell or tissue-specific transforming constructs of the present invention can be specifically delivered into a target cell or tissue in a similar manner.

In another example, lactosyl ceramide, and peptides that target the LDL receptor related proteins, such as apolipoprotein E3 ("Apo E") have been useful in targeting liposomes to the liver (Spanjer and Scherphof, 1983; WO 98/0748).

Folate and the folate receptor have also been described as useful for cellular targeting (U.S. Pat. No. 5,871,727). In this example, the vitamin folate is coupled to the complex. The folate receptor has high affinity for its ligand and is overexpressed on the surface of several malignant cell lines, including lung, breast and brain tumors. Anti-folate such as methotrexate may also be used as targeting ligands. Transferrin mediated delivery systems target a wide range of replicating cells that express the transferrin receptor (Gilliland et al., 1980).

12. Liposome/Nucleic Acid Combinations

In certain embodiments, a liposome/SRF composition may comprise a nucleic acid, such as, for example, an oligonucleotide, a polynucleotide or a nucleic acid construct (e.g., an expression vector). Where a bacterial promoter is employed in the DNA construct that is to be transfected into eukaryotic cells, it also will be desirable to include within the liposome an appropriate bacterial polymerase.

It is contemplated that when the liposome/SRF composition comprises a cell or tissue specific nucleic acid, this technique may have applicability in the present invention. In certain embodiments, lipid-based non-viral formulations provide an alternative to viral gene therapies. Although many cell culture studies have documented lipid-based non-viral gene transfer, systemic gene delivery via lipid-based formulations has been limited. A major limitation of non-viral lipid-based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in liposome stability in the presence and absence of serum proteins. The interaction between liposomes and serum proteins has a dramatic impact on the stability characteristics of liposomes (Yang and Huang, 1997). Cationic liposomes attract and bind negatively charged serum proteins. Liposomes coated by serum proteins are either dissolved or taken up by macrophages leading to their removal from circulation. Current in vivo liposomal delivery methods use aerosolization, subcutaneous, intradermal, intratumoral, or intracranial injection to avoid the toxicity and stability problems associated with cationic lipids in the circulation. The interaction of liposomes and plasma proteins is largely responsible for the disparity between the efficiency of in vitro (Felgner et al., 1987) and in vivo gene transfer (Zhu et al., 1993; Philip et al., 1993; Solodin et al., 1995; Liu et al., 1995; Thierry et al., 1995; Tsukamoto et al., 1995; Aksentijevich et al., 1996).

An exemplary method for targeting viral particles to cells that lack a single cell-specific marker has been described (U.S. Pat. No. 5,849,718). In this method, for example, antibody A may have specificity for tumor, but also for normal heart and lung tissue, while antibody B has specificity for tumor but also normal liver cells. The use of antibody A or antibody B alone to deliver an anti-proliferative nucleic acid to the tumor would possibly result in unwanted damage to heart and lung or liver cells. However, antibody A and antibody B can be used together for improved cell targeting. Thus, antibody A is coupled to a gene encoding an anti-proliferative nucleic acid and is delivered, via a receptor mediated uptake system, to tumor as well as heart and lung tissue. However, the gene is not transcribed in these cells as they lack a necessary transcription factor. Antibody B is coupled to a universally active gene encoding the transcription factor necessary for the transcription of the anti-proliferative nucleic acid and is delivered to tumor and liver cells. Therefore, in heart and lung cells only the inactive anti-proliferative nucleic acid is delivered, where it is not transcribed, leading to no adverse effects. In liver cells, the gene encoding the transcription factor is delivered and transcribed, but has no effect because no an anti-proliferative nucleic acid gene is present. In tumor cells, however, both genes are delivered and the transcription factor can activate transcription of the anti-proliferative nucleic acid, leading to tumor-specific toxic effects.

The addition of targeting ligands for gene delivery for the treatment of hyperproliferative diseases permits the delivery of genes whose gene products are more toxic than do non-targeted systems. Examples of the more toxic genes that can be delivered includes pro-apoptotic genes such as Bax and Bak plus genes derived from viruses and other pathogens such as the adenoviral E4orf4 and the *E. coli* purine nucleoside phosphorylase, a so-called "suicide gene" which converts the prodrug 6-methylpurine deoxyriboside to toxic purine 6-methylpurine. Other examples of suicide genes used with prodrug therapy are the *E. coli* cytosine deaminase gene and the HSV thymidine kinase gene.

It is also possible to utilize untargeted or targeted lipid complexes to generate recombinant or modified viruses in vivo. For example, two or more plasmids could be used to introduce retroviral sequences plus a therapeutic gene into a hyperproliferative cell. Retroviral proteins provided in trans from one of the plasmids would permit packaging of the second, therapeutic gene-carrying plasmid. Transduced cells, therefore, would become a site for production of non-replicative retroviruses carrying the therapeutic gene. These retroviruses would then be capable of infecting nearby cells. The promoter for the therapeutic gene may or may not be inducible or tissue specific.

Similarly, the transferred nucleic acid may represent the DNA for a replication competent or conditionally replicating viral genome, such as an adenoviral genome that lacks all or part of the adenoviral E1a or E2b region or that has one or more tissue-specific or inducible promoters driving transcription from the E1a and/or E1b regions. This replicating or conditional replicating nucleic acid may or may not contain an additional therapeutic gene such as a tumor suppressor gene or anti-oncogene.

13. Lipid Administration

The actual dosage amount of a lipid composition (e.g., a liposome- SRF composition) administered to a patient can be determined by physical and physiological factors such as body weight, severity of condition, idiopathy of the patient and on the route of administration. With these considerations in mind, the dosage of a lipid composition for a particular subject and/or course of treatment can readily be determined.

The present invention can be administered intravenously, intradermally, intraarterially, intraperitoneally, intralesionally, intracranially, intraarticularly, intraprostaticaly, intrapleurally, intratracheally, intranasally, intravitreally, intravaginally, rectally,topically, intratumorally, intramuscularly, subcutaneously, intravesicularlly, mucosally, intrapericardially, orally, topically, locally and/or using aerosol, injection, infusion, continuous infusion, localized perfusion bathing target cells directly or via a catheter and/or lavage.

IX. Screening for Modulators of the Protein Function

The present invention further comprises methods for identifying modulators of the function of SRF, such as identifying modulators of SRF cleavage. These assays may comprise random screening of large libraries of candidate substances; alternatively, the assays may be used to focus on particular classes of compounds selected with an eye towards structural attributes that are believed to make them more likely to modulate the function of SRF or cleavage thereof.

By function, it is meant that one may assay, for example, the ability to inhibit expression of SRF, inhibit activity of SRF, inhibit cleavage of SRF, or a combination thereof. One may also assay for more global effects, such as amelioration and/or prevention of at least one cardiac disease symptom.

To identify a SRF modulator, one generally will characterize the function, activity, expression, or cleavage status of SRF in the presence and absence of the candidate substance, a modulator defined as any substance that alters function. For example, a method generally comprises:

providing a candidate modulator;

admixing the candidate modulator with an isolated compound or cell, or a suitable experimental animal;

measuring one or more characteristics of the compound, cell or animal in step (c); and comparing the characteristic measured in step (c) with the characteristic of the compound, cell or animal in the absence of said candidate modulator, wherein a difference between the measured characteristics indicates that said candidate modulator is, indeed, a modulator of the compound, cell or animal.

Assays may be conducted in cell free systems, in isolated cells, or in organisms including transgenic animals.

It will, of course, be understood that all the screening methods of the present invention are useful in themselves notwithstanding the fact that effective candidates may not be found. The invention provides methods for screening for such candidates, not solely methods of finding them.

A. Modulators

As used herein the term "candidate substance" refers to any molecule that may potentially inhibit SRF expression, function, activity, or cleavage status. The candidate substance may be a protein or fragment thereof, a small molecule, or even a nucleic acid molecule. It may prove to be the case that the most useful pharmacological compounds will be compounds that are structurally related to inhibitors of similar compounds. Using lead compounds to help develop improved compounds is know as "rational drug design" and includes not only comparisons with know inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

An inhibitor according to the present invention may be one that exerts its inhibitory or activating effect upstream, downstream or directly on SRF. Regardless of the type of inhibitor or activator identified by the present screening methods, the effect of the inhibition or activator by such a compound results in inhibition of SRF expression, activity, function, cleavage status, or amelioration and/or prevention of at least one cardiac disease symptom as compared to that observed in the absence of the added candidate substance.

B. In Vitro Assays

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule in a specific fashion is strong evidence of a related biological effect. For example, binding of a molecule to a target may, in and of itself, be inhibitory, due to steric, allosteric or charge-charge interactions. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

C. In Cyto Assays

The present invention also contemplates the screening of compounds for their ability to modulate SRF or cleavage thereof in cells. Various cell lines can be utilized for such screening assays, including cells specifically engineered for this purpose. In a particular exemplary embodiment, cardiac cells are utilized and, in further specific exemplary embodiments, SRF is cleaved in the cell. In specific embodiments, apoptosis of the cell is assayed.

Depending on the assay, culture may be required. The cell is examined using any of a number of different physiologic assays. Alternatively, molecular analysis may be performed, for example, looking at protein expression, mRNA expression (including differential display of whole cell or polyA RNA) and others.

D. In Vivo Assays

In vivo assays involve the use of various animal models, including transgenic animals that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more candidate substances are administered to an animal, and the ability of the candidate substance(s) to alter one or more characteristics, as compared to a similar animal not treated with the candidate substance(s), identifies a modulator. The characteristics may be any of those discussed above with regard to the function of a particular compound (e.g., enzyme, receptor, hormone) or cell (e.g., growth, tumorigenicity, survival), or instead a broader indication such as behavior, anemia, immune response, etc.

The present invention provides methods of screening for a candidate substance that inhibits SRF expression, activity, function, or cleavage or that ameliorates and/or prevents at least one symptom of cardiac disease. In particular embodiments, the present invention is directed to a method for determining the ability of a candidate substance to inhibit SRF cleavage, generally including the steps of: administering a candidate substance to the animal; and determining the ability of the candidate substance to reduce one or more characteristics of cardiac disease.

Treatment of these animals with test compounds will involve the administration of the compound, in an appropriate form, to the animal. Administration will be by any route that could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in vitro or in cyto assays.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Exemplary Methods and Materials

Human Failing Heart Tissues

Myocardial samples were obtained from 13 patients with end-stage heart failure at the time of transplant: seven patients had ischemic cardiomyopathy (ICM); five patients had dilated cardiomyopathy (DCM); and one had hypertrophic cardiomyopathy (HCM). An additional ten patients with end-stage heart failure including 8 DCM and 2 ICM had been maintained on LVAD until transplant. Samples were obtained from 7 patients who died of non-cardiac causes, as a control group. Left ventricular ejection fraction was less than 20% in all heart failure patients. All protocols were approved by the Institutional Review Board of Baylor College of Medicine.

Plasmid Constructs

The construction and use of reporter plasmids containing the skeletal (SK-luc) and cardiac α-actin (aCA-luc) promoters linked to luciferase reporters were as previously described (MacLellan et al., 1994; Wei et al., 1998). The vector pCGN, a cytomegalovirus promoter-driven expression vector, was used to express full length SRF (residues 1-508) (pCGN-SRF), N-terminal SRF (residues 1-254) (pCGN-SRF-N), C-terminal SRF (residues 255-508) (pCGN-SRF-C) and SRFpm1 (pCGN-SRFpm1) containing triple point mutants within the MADS box (Prywes and Zhu, 1992).

Cell Cultures, Plasmid DNA Transfection, and Reporter Gene Assays

C2C12 myoblasts and neonatal rat cardiomyocytes were cultured as previously described (MacLellan et al., 1994; Wei et al., 1998). Cells plated in 30-mm plates were transfected with 0.6 mg of total plasmid DNA containing the reporter plasmid (SK-luc or aCA-luc) and the indicated expression plasmids. Transfections were performed using LipofectAMINE (Invitrogen) according to the manufacturer's instructions. Cells were harvested 40 h post-transfection and luciferase activity was measured as previously described (MacLellan et al., 1994).

Western Blot Analysis

An anti-SRF N-terminal antibody (anti-SRF-N) was made (Bethyl Laboratories, Inc.) using the peptide sequence GANGGRVPGNGA (SEQ ID NO:5), a portion of exon 1 domain of SRF from human origin. The antibody was purified by affinity chromatography and tested by ELISA. An anti-SRF C-terminal antibody (anti-SRF-C) was purchased from Santa Cruz (sc-335), which reacts against a portion of exon 7 domain of SRF. These antibodies were first tested against SRF-N, SRF-C and full length of SRF expressed in transfected CV1 cells. An anti-caspase 3 antibody, which reacts with both precursor and active subunits, was purchased from Santa Cruz (sc-7148). Protein samples from myocardial tissues were prepared as previously described (Chang et al., 2000). Total protein (40 mg) was separated by Invitrogen 12% NuPAGE Bis-Tris ready gel, and then transferred to nitrocellulose. The membrane was probed with specific antibodies described above, and immunoreactive bands were visualized with Pierce's Supersignal West Pico chemiluminescence. Even loadings were confirmed by Ponceau staining.

Immunofluorescence Analysis

Visualization of transfected SRF and SRF-N cellular localization was implemented in neonatal cardiomyocytes attached to coverslips as described previously (Wei et al., 2001). Anti-HA antibody was used at 1:200.

Electrophoretic Gel Mobility Shift Assay (EMSA)

DNA binding activity of SRF-N was assayed by EMSA with recombinant SRF-N and full length SRF and with the oligonucleotide probe corresponding to the proximal SRE1 of the skeletal a-actin promoter as previously described (MacLellan et al., 1994; Wei et al., 1998). Recombinant SRF and SRF-N were generated using pET-15b (Novagen) vector, which contains 6'histidine tag. These recombinant SRFs were expressed in BL21 (Stratagene) competent cells followed by Ni-NTA (nickel-nitrilotriacetic acid) resin purification.

In Vitro Cleavage of SRF by Caspase

Recombinant purified full length SRF was incubated with active recombinant human caspase 3 (BD PharMingen) in the presence or absence of 20 µM of Z-VAD-fmk (BD PharMingen), a caspase 3 inhibitor, in a reaction buffer (50 mM HEPES (pH 7.4), 100 mM NaCl, 1 mM EDTA, 0.1% CHAPS, 10 mM DTT and 10% glycerol). Reactions were analyzed by Western blot as described above.

Statistical Analysis

Data were analyzed by one-way analysis of variance (ANOVA), followed by the Krustal-Wallis one-way analysis of variance on ranks (SigmaStat software, SPSS Inc., Chicago, Ill.). A p<0.05 was considered significant. Data are presented as mean±SEM.

Example 2

SRF Cleaved by Caspase 3 and SRF Subfragments Accumulates in Cardiac Tissues Obtained from Patients with End-stage Heart Failure and Reversed by LVAD Marked reduction of full length SRF (65 kDa; FIG. 1) was observed, accompanied by the appearance of two smaller fragments with molecular weights 55 kDa and 32 kDa) in samples taken from failing hearts (FIG. 1A). Normal hearts contained barely-detectable cleavage products. These data were next compared with five representative samples taken from the hearts of patients with equivalent heart failure who had been placed on a LVAD. The amount of SRF cleavage was strikingly reduced, and a substantial portion of the 65 kDa full length SRF remained intact (FIGS. 1A and 1B). In fact, SRF cleavage in the LVAD group did not differ significantly from the control (FIG. 1B). Based on previous studies with apoptosis, (Drewett et al., 2001; Bertolotto et al., 2000), the inventors postulated that the SRF cleavage was effected by caspase 3. These results indicated that the protein expression profile of SRF is markedly altered in human failing hearts, and this process is reversed by LVAD support.

It was also observed that these failing hearts had increased activated caspase 3 levels when compared to either the normal hearts or the failing hearts with LVAD support (FIG. 1C). The precursor level of caspase 3 was not significantly different among normal, failing and LVAD-supported hearts. Thus, the data suggest a correlation between the increased activated caspase 3 levels in the failing hearts and the proteolytic processing of full length SRF with the concomitant appearance of SRF sub-species.

Example 3

In Vitro Cleavage of SRF with Active Caspase 3

Figure 2:
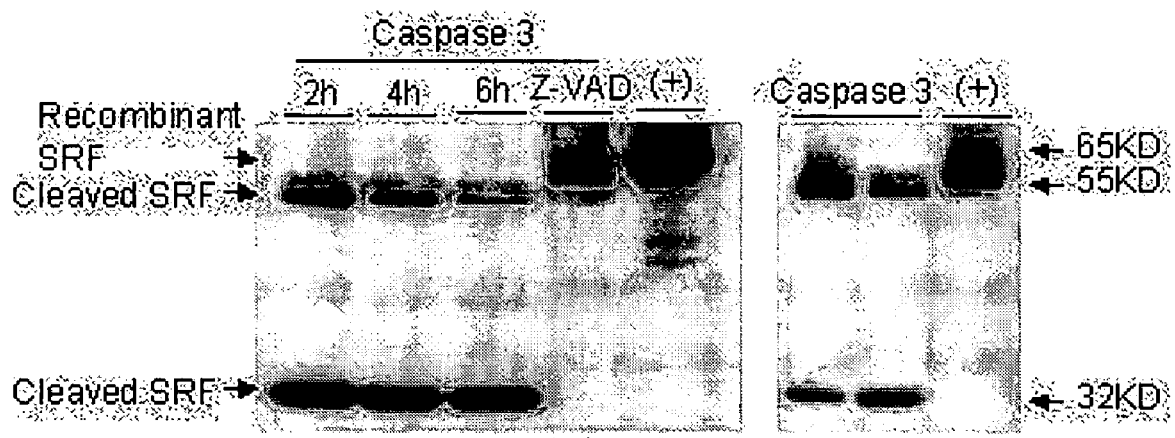
FIG. 2 demonstrates that recombinant SRF was cleaved by active caspase 3 in vitro. Two fragments of 55 and 32 kDa were observed, which corresponded in size to those detected in human failing hearts. The cleavage was blocked by caspase 3 inhibitor, Z-VAD.

To examine caspase 3 cleavage of SRF, we incubated activated caspase 3 with recombinant SRF in vitro. In FIG. 2 (left panel), the time course of caspase proteolysis is demonstrated. Caspase 3 cleaved SRF in a time-dependent manner, and this cleavage was inhibited by the caspase inhibitor, Z-VAD. Examination of the time course demonstrated that the 55 kDa fragment tended to disappear over 6 hours while the 32 kDa fragment slightly increased. In FIG. 2 (right panel), a similar relationship was seen with increasing concentration of activated caspase 3. In this case, the 55 kDa fragment tended to fall as a function of caspase 3 doses while there was a coincident increase into a 32 kDa fragment.

Example 4

Figure 3:
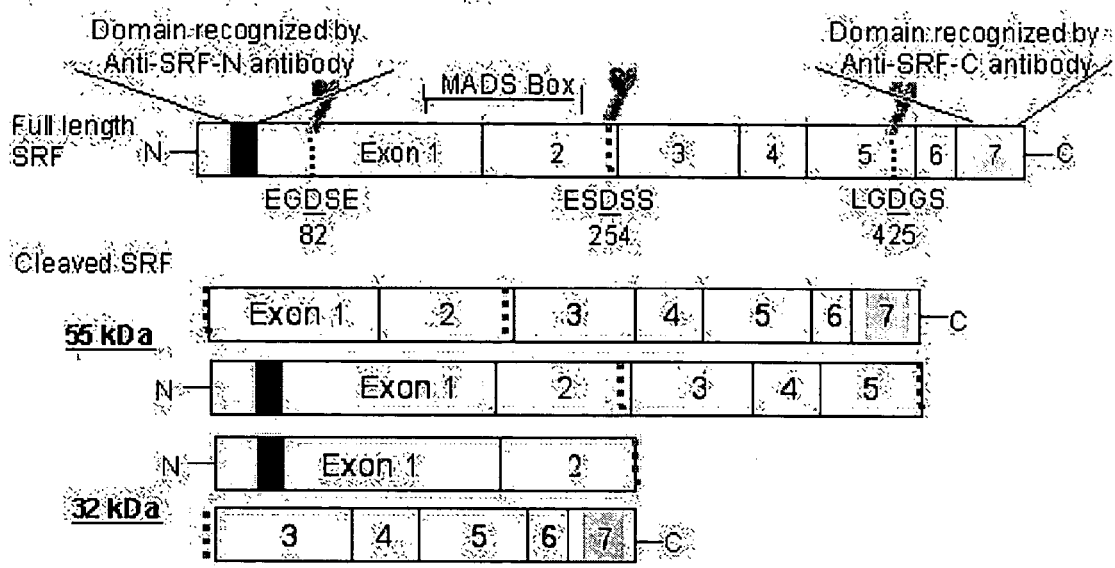
FIGS. 3A through 3C show SRF caspase 3 cleavage documented by specific N and C terminal immunoreactivity of samples taken from failing hearts.
Figure 3:
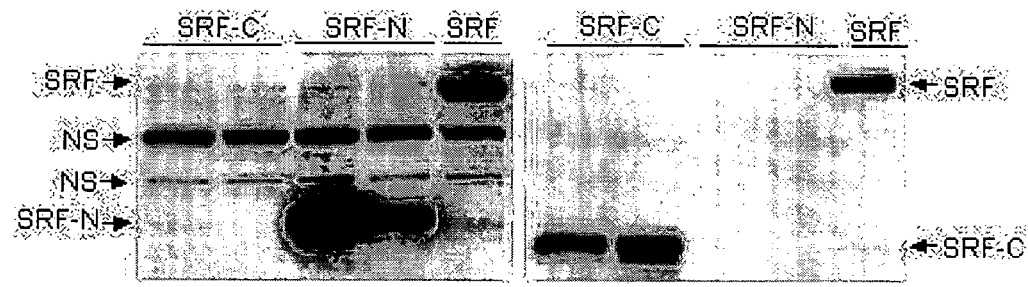
Figure 3:
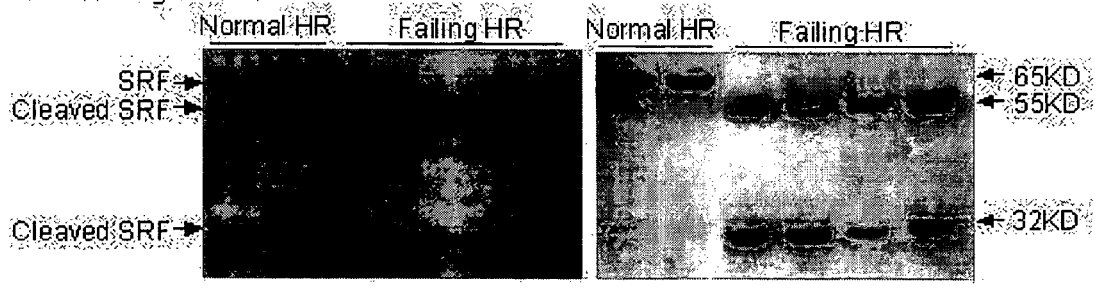

Caspase 3 Cleavage of SRF is Defined by N-terminal and C-terminal Specific Antibodies SRF appears to be initially cleaved to a 55 kDa fragment and subsequently cleaved to a 32 kDa subfragment. Examination of the sequence of SRF revealed aspartates at the 82nd and 425th amino acids, cleavage at which would be expected to generate a 55 kDa fragment. In each case, the subsequent cleavage at aspartate254, would yield a 32 kDa fragment, as we observed. Thus there would be two 55 kDa and two 32 kDa, as shown in the schematic diagram in FIG. 3A. To further examine this, specific antibodies directed to the N-terminus or C-terminus of SRF were used. As shown in FIG. 3B, anti-SRF-N and anti-SRF-C detected SRF-N and SRF-C fragments respectively, as well as full length of SRF indicating specific recognition. It was observed that the 55 kDa fragment and the 32 kDa fragment found in heart failure samples reacted with both of these antibodies (FIG. 3C). Thus, initial cleavages occur at asp82 and asp425, but apparently not both in the same molecule. This initial cleavage is followed by a cleavage at asp254, which generates two different 32 kDa fragments, one containing the N-terminal (SRF-N) and one containing the C-terminal (SRF-C) fragments as shown in the failing hearts (FIG. 3C).

Example 5

Figure 4:
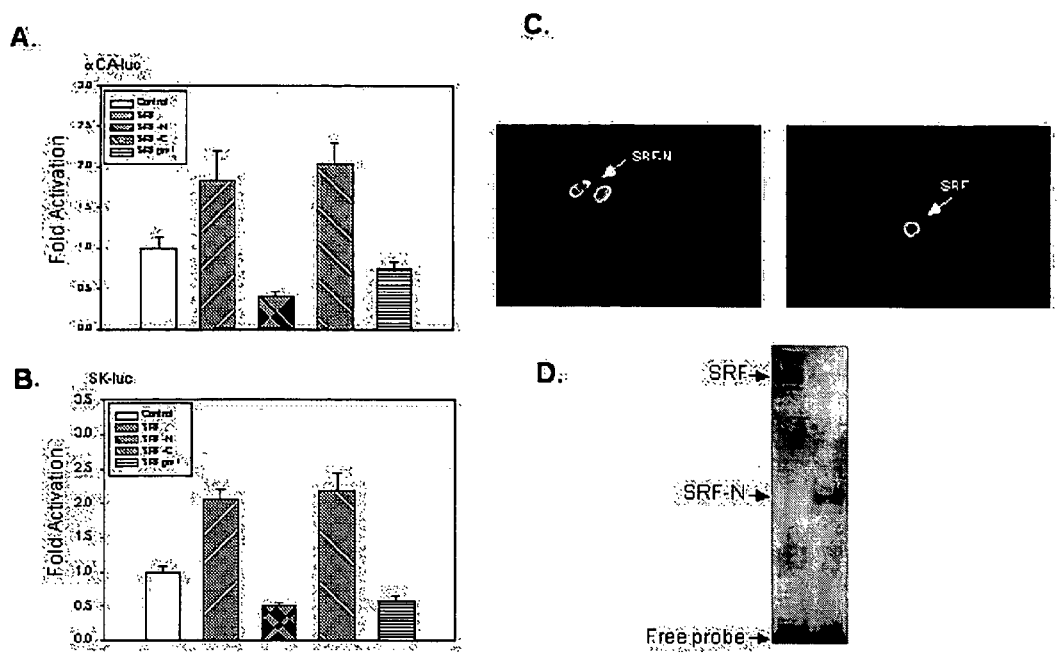
FIGS. 4A through 4D show that cleaved SRF-N fragment is a dominant negative transcription factor.

SRF-N Serves as a Dominant Negative Inhibitor of Muscle Specific Gene Transcription To evaluate potential functional significance of the cleaved fragments, we overexpressed the SRF-N and SRF-C fragments via CMV promoter-driven expression plasmids co-transfected with cardiac α-actin and skeletal α-actin promoter reporter plasmids in cultured rat neonatal cardiomyocytes and C2C12 myoblasts. As shown in FIGS. 4A and 4B, SRF-N decreased the basal transcriptional activities of the cardiac α-actin and the skeletal α-actin promoter by 60% and 50% in cardiomyocytes and in C2C12 myoblasts, respectively, indicating that this fragment functioned as a dominant negative inhibitor of SRF dependent transcription. This inhibitory effect was very similar to that observed by a SRF negative mutant SRFpml (Wei et al., 1998; Prywes and Zhu, 1992; Johansen and Prywes, 1993). In contrast, the 32 kDa fragment from C-terminal, SRF-C, did not inhibit actin promoter activity. FIG. 4C shows immunofluorescence of SRF wildtype and SRF-N in the nuclei of transfected cardiac myocytes, indicating the capability of SRF-N to localize to myogenic nuclei. As shown in FIG. 4D, SRF-N fragment bound to skeletal α-actin SRE1 DNA probe in an EMSA, as observed for full length recombinant SRF, indicating that SRF-N retains DNA binding activity and could compete with the endogenous SRF for binding to SREs, the DNA target sequences.

Example 6

Significance of the Present Invention

SRF cleavage occurs in the myocytes of the severely failing heart. Previous work in cell culture has suggested that cleavage of SRF associated with apoptosis and its mediation by caspase (Drewett et al., 2001; Bertolotto et al., 2000). Moretti and co-workers (Moretti et al., 2002) have demonstrated caspase 3 meditated cleavage of myosin light chains in failing myocardium. They have suggested that cleavage of cardiac specific proteins may be part of the course of severe heart failure (Moretti et al., 2002). The present inventors, however, show: 1) application to human heart failure, 2) potential reversibility of the caspase induced proteolytic cascade (with regard to SRF); and 3) amplified the impact of SRF cleavage by virtue of the loss of a critical transcriptional modifier which regulates many cardiac genes as well as the generation of its dominant negative inhibitor.

Since these data are from human hearts, the concept of reversibility can only be inferred. The data suggests that this is a universal mechanism seen in human heart failure but does not speak to the pathological conditions which might mediate caspase activation. The data herein regarded a group of patients who had equivalently severe heart failure but whom had been treated with LVAD as a bridge to transplant. The only difference between the two groups was whether or not the LVAD was inserted; all were sampled at the time of transplant. The results demonstrated that the cardiac tissue in the LVAD group demonstrated virtually no loss of SRF; the fragmentation was not significantly different from a control group. There is no question that both groups had severe heart failure and that the LVAD did not cure the reason for failing myocardium; it merely unloaded the ventricle (by partially supporting the circulation). Thus, in a specific embodiment, the caspase activation is induced as a result of myocardial mechanical overload and the reduction of this load results in a clearing of activated caspase3 and synthesis of new SRF. In an alternative embodiment, ventricular overload induces apoptosis and the caspase3 activation is part of the apoptotic cascade leading to cell death. The cells that die are cleared and the cells remaining do not have activated caspase3 because they had not gone into apoptosis. Given the very large percent of the SRF that is fragmented in these samples, however, it seems unlikely that all the cells that contain fragmented SRF are ultimately going into apoptosis; the patient would survive only a matter of days. In a specific embodiment, the mitochondria dysfunction frequently reported associated with heart failure releases cytochrome c and initiates a more limited version of the caspase activation pathway leading to apoptosis.

Severe heart failure is associated with reduction of many cardiac specific genes and the possibility that they have been proteolytically cleaved have been previously proposed (Narula et al., 1999). The number of genes suppressed is quite large and the mechanism by which proteins would be chosen for proteolysis and the specificity of those choices has not been extensively studied. The present invention provides an embodiment in which specific cleavage of a transcription factor results in an amplified effect on cardiac specific genes by suppressing entire groups of genes that depend on SRF for cardiac specific transcription. Regulatory regions of a number of muscle specific genes and other myogenic specified genes contain CArG boxes or serum response elements as part of their promoter activity and depend upon SRF activity (Johansen and prywes, 1993; Talanian et al., 1997). Mutations that prevent SRF binding severely impair the expression of c-fos and other immediate early growth genes, as well as, these muscle restricted contractile protein genes (Lee et al., 1992; Li et al., 1997). In addition, there is a known naturally occurring, alternatively spliced mutant SRF that functions as a dominant negative inhibitor in vivo (Boxer et al., 1989; Lee et al., 1991).

There are two mechanisms involved in the repression of SRF dependent gene activation. In the first place, there is a striking reduction in full length SRF in these cells. In addition, the SRF-N is similar in composition to the naturally occurring dominant negative (Boxer et al., 1989; Lee et al., 1991). These fragments contain intact MADS box but do not contain the C-terminal transactivation domain, so that high levels of the truncated fragment compete with full length SRF as either homodimers or heterodimers for binding to the serum response element. Without the transactivation domain, the truncated SRF binds but does not activate transcription; it is a dominant negative inhibitor.

Another striking feature of these studies is the apparent reversibility of this process by ventricular unloading. Given that it is possible that long-term caspase inhibition has many hazards, since apoptosis is a beneficial part of many biological processes, in specific embodiments intermittent short-term treatment with caspase inhibitors provide beneficial effects on reducing cleavage of vital transcription regulatory factors.

REFERENCES

All patents and publications mentioned in the specification are indicative of the levels of those skilled in the art to which the invention pertains. All patents and publications are herein incorporated by reference to the same extent as if each individual publication was specifically and individually indicated to be incorporated by reference.

PUBLICATIONS

Barrans J D, Allen P D, Stamatiou D, Dzau V J, Liew C C. Global gene expression profiling of end-stage dilated cardiomyopathy using a human cardiovascular-based cDNA microarray. Am J Pathol 2002; 160:2035-43.

Belaguli N S, Sepulveda J L, Nigam V, Charron F, Nemer M, Schwartz R J. Cardiac tissue enriched factors serum response factor and GATA-4 are mutual coregulators. Mol Cell Biol 2000; 20:7550-8.

Belaguli N S, Zhou W, Trinh T H, Majesky M W, Schwartz R J. Dominant negative murine serum response factor: alternative splicing within the activation domain inhibits transactivation of serum response factor binding targets. Mol Cell Biol 1999; 19:4582-91.

Bertolotto C, Ricci J E, Luciano F, Mari B, Chambard J C, Auberger P. Cleavage of the serum response factor during death receptor-induced apoptosis results in an inhibition of the c-FOS promoter transcriptional activity. J Biol Chem 2000; 275:12941-7.

Boxer L M, Prywes R, Roeder R G, Kedes L. The sarcomeric actin CArG-binding factor is indistinguishable from the c-fos serum response factor. Mol Cell Biol 1989; 9:515-22.

Chen C Y, Schwartz R J. Recruitment of the tin man homolog Nkx-2.5 by serum response factor activates cardiac alph-actin gene transcription. Mol Cell Biol 1996; 16:6372-84.

Drewett V, Devitt A, Saxton J, et al. Serum response factor cleavage by caspases 3 and 7 linked to apoptosis in human BJAB cells. J Biol Chem 2001; 276:33444-51.

Emoto Y, Manome Y, Meinhardt G, et al. Proteolytic activation of protein kinase C delta by an ICE-like protease in apoptotic cells. Embo J 1995; 14:6148-56.

Gottlieb R A, Burleson K O, Kloner R A, Babior B M, Engler R L. Reperfusion injury induces apoptosis in rabbit cardiomyocytes. J Clin Invest 1994; 94:1621-8.

Haunstetter A, Izumo S. Apoptosis: basic mechanisms and implications for cardiovascular disease. Circ Res 1998; 82:1111-29.

Hwang J J, Allen P D, Tseng G C, et al. Microarray gene expression profiles in dilated and hypertrophic cardiomyopathic end-stage heart failure. Physiol Genomics 2002; 10:31-44. Hirota H, Chen J, Betz U A, et al. Loss of a gp130 cardiac muscle cell survival pathway is a critical event in the onset of heart failure during biomechanical stress. Cell 1999; 97:189-98.

Johansen F E, Prywes R. Identification of transcriptional activation and inhibitory domains in serum response factor (SRF) by using GAL4-SRF constructs. Mol Cell Biol 1993; 13:4640-7. Kang P M, Izumo S. Apoptosis and heart failure: A critical review of the literature. Circ Res 2000; 86:1107-13.

Lee T C, Chow K L, Fang P, Schwartz R J. Activation of skeletal alpha-actin gene transcription: the cooperative formation of serum response factor-binding complexes over positive cis-acting promoter serum response elements displaces a negative-acting nuclear factor enriched in replicating myoblasts and nonmyogenic cells. Mol Cell Biol 1991; 11:5090-100.

Lee T C, Shi Y, Schwartz R J. Displacement of BrdUrd-induced YY1 by serum response factor activates skeletal alpha-actin transcription in embryonic myoblasts. Proc Natl Acad Sci USA 1992; 89:9814-8.

Li L, Liu Z, Mercer B, Overbeek P, Olson E N. Evidence for serum response factor-mediated regulatory networks governing SM22alpha transcription in smooth, skeletal, and cardiac muscle cells. Dev Biol 1997; 187:311-21. MacLellan W R, Lee T C, Schwartz R J, Schneider M D. Transforming growth factor-beta response elements of the skeletal alpha-actin gene. Combinatorial action of serum response factor, YY1, and the SV40 enhancer-binding protein, TEF-1. J Biol Chem 1994; 269:16754-60.

Moretti A, Weig H J, Ott T, et al. Essential myosin light chain as a target for caspase-3 in failing myocardium. Proc Natl Acad Sci USA 2002.

Narula J, Pandey P, Arbustini E, et al. Apoptosis in heart failure: release of cytochrome c from mitochondria and activation of caspase-3 in human cardiomyopathy. Proc Natl Acad Sci USA 1999; 96:8144-9.

Narula J, Haider N, Virmani R, et al. Apoptosis in myocytes in end-stage heart failure. N Engl J Med 1996; 335:1182-9.

Narula J, Hajjar R J, Dec G W. Apoptosis in the failing heart. Cardiol Clin 1998; 16:691-710, ix.

Narula J, Kharbanda S, Khaw B A. Apoptosis and the heart. Chest 1997; 112:1358-62.

Prywes R, Zhu H. In vitro squelching of activated transcription by serum response factor: evidence for a common coactivator used by multiple transcriptional activators. Nucleic Acids Res 1992; 20:513-20.

Razeghi P, Young M E, Cockrill T C, Frazier O H, Taegtmeyer H. Downregulation of myocardial myocyte enhancer factor 2C and myocyte enhancer factor 2C-regulated gene expression in diabetic patients with nonischemic heart failure. Circulation 2002; 106:407-11.

Scarabelli T, Stephanou A, Rayment N, et al. Apoptosis of endothelial cells precedes myocyte cell apoptosis in ischemia/reperfusion injury. Circulation 2001; 104:253-6.

Scarabelli T M, Stephanou A, Pasini E, et al. Different signaling pathways induce apoptosis in endothelial cells and cardiac myocytes during ischemia/reperfusion injury. Circ Res 2002; 90:745-8. Wei L, Wang L, Carson J A, Agan J E, Imanaka-Yoshida K, Schwartz R J. beta1 integrin and organized actin filaments facilitate cardiomyocyte-specific RhoA-dependent activation of the skeletal alpha-actin promoter. Faseb J 2001; 15:785-96.

Sebbagh M, Renvoize C, Hamelin J, Riche N, Bertoglio J, Breard J. Caspase-3-mediated cleavage of ROCK I induces MLC phosphorylation and apoptotic membrane blebbing. Nat Cell Biol 2001; 3:346-52.

Sepulveda J L, Vlahopoulos S, Iyer D, Belaguli N, Schwartz R J. Combinatorial expression of GATA4, Nkx2-5, and serum response factor directs early cardiac gene activity. J Biol Chem 2002; 277:25775-82.

Wei L, Zhou W, Croissant J D, et al. RhoA signaling via serum response factor plays an obligatory role in myogenic differentiation. J Biol Chem 1998; 273:30287-94.

Zhang X, Chai J, Azhar G, et al. Early postnatal cardiac changes and premature death in transgenic mice overexpressing a mutant form of serum response factor. J Biol Chem 2001; 276:40033-40.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim:

1. A method of diagnosing cardiac disease resulting from apoptosis in an individual, comprising the step of identifying cleavage of SRF in at least one cardiac cell from a sample from said individual, wherein identifying said SRF cleavage fragment indicates a diagnosis of cardiac disease resulting from apoptosis.

2. The method of claim 1, wherein the sample is from a tissue of the individual.

3. The method of claim 1, wherein the cardiac cell is from ventricular tissue.

4. The method of claim 1, wherein the identifying step further comprises
comparing levels of cleaved SRF in a sample from an individual suspected of having cardiac failure with a known control reflective of levels of cleaved SRF in non-failing cardiac tissue, wherein when said sample comprises elevated levels of cleaved SRF compared to said control, said individual suspected of having cardiac failure has a positive diagnosis for cardiac failure.

5. The method of claim 4, wherein the identifying step comprises immunoblot analysis for said cleaved SRF.

6. The method of claim 5, wherein the immunoblot analysis comprises an antibody against a region of SRF.

7. The method of claim 6, wherein the region of SRF is an N-terminal region or a C-terminal region.

8. The method of claim 7, wherein the N-terminal region comprises at least a portion of amino acid sequence encoded by the first coding exon of a SRF polynucleotide.

9. The method of claim 7, wherein the region of SRF comprises SEQ ID NO:5.

10. The method of claim 1, wherein said cardiac disease is further defined as cardiac failure.

* * * * *

UNITED STATES PATENT AND TRADEMARK OFFICE
CERTIFICATE OF CORRECTION

PATENT NO. : 7,582,478 B2  Page 1 of 1
APPLICATION NO. : 10/763037
DATED : September 1, 2009
INVENTOR(S) : Schwartz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 574 days.

Signed and Sealed this

Fourteenth Day of September, 2010

David J. Kappos
*Director of the United States Patent and Trademark Office*